(12) United States Patent
Phadte et al.

(10) Patent No.: US 9,723,840 B2
(45) Date of Patent: Aug. 8, 2017

(54) 1-(PYRIDAZIN-3-YL)-IMIDAZOLIDIN-2-ONE DERIVATIVES AS HERBICIDES

(71) Applicants: SYNGENTA PARTICIPATIONS AG, Basel (CH); SYNGENTA LIMITED, Guildford, Surrey (GB)

(72) Inventors: Mangala Phadte, Ilhas (IN); Ravindra Sonawane, Ilhas (IN); Adrian Longstaff, Bracknell (GB); Kenneth Ling, Bracknell (GB); Sally Elizabeth Russell, Bracknell (GB); Timothy Robert Desson, Bracknell (GB); Matthew Brian Hotson, Bracknell (GB); Donn Warwick Moseley, Bracknell (GB); Jutta Elisabeth Boehmer, Bracknell (GB); James Alan Morris, Bracknell (GB); Alan Joseph Hennessy, Bracknell (GB)

(73) Assignees: Syngenta Limited, Guikdford, Surrey (GB); Syngetna Participations AG, Base (CH)

( * ) Notice: Subject to any disclaimer, the term of this patent is extended or adjusted under 35 U.S.C. 154(b) by 0 days.

(21) Appl. No.: 15/035,665

(22) PCT Filed: Nov. 6, 2014

(86) PCT No.: PCT/EP2014/073943
§ 371 (c)(1),
(2) Date: May 10, 2016

(87) PCT Pub. No.: WO2015/067701
PCT Pub. Date: May 14, 2015

(65) Prior Publication Data
US 2016/0262395 A1    Sep. 15, 2016

(30) Foreign Application Priority Data
Nov. 11, 2013  (IN) .......................... 3309/DEL/2013

(51) Int. Cl.
*A01N 43/58*  (2006.01)
*C07D 403/04*  (2006.01)

(52) U.S. Cl.
CPC .......... *A01N 43/58* (2013.01); *C07D 403/04* (2013.01)

(58) Field of Classification Search
CPC ............................ A01N 43/58; C07D 403/04
See application file for complete search history.

(56) References Cited

U.S. PATENT DOCUMENTS 4,604,127 A  *  8/1986  Abdulla ............... C07D 403/04
                                                    504/237

FOREIGN PATENT DOCUMENTS

| EP | 0169050    | * | 1/1986 | .......... C07D 403/04 |
| EP | 0169050 A2 |   | 1/1986 | |

OTHER PUBLICATIONS

International Search Report for International Application No. PCT/EP2014/07394, mailed Nov. 6, 2014.

* cited by examiner

*Primary Examiner* — Alton Pryor
(74) *Attorney, Agent, or Firm* — James Cueva

(57) ABSTRACT

The invention relates to pyrrolone compounds of the formula (I) wherein $R^1$, $R^2$, $R^3$, $R^b$, $R^c$ and $R^d$ are as defined in the specification. Furthermore, the present invention relates to processes and intermediates for making compounds of formula (I), to herbicidal compositions comprising these compounds and to methods of using these compounds to control plant growth.

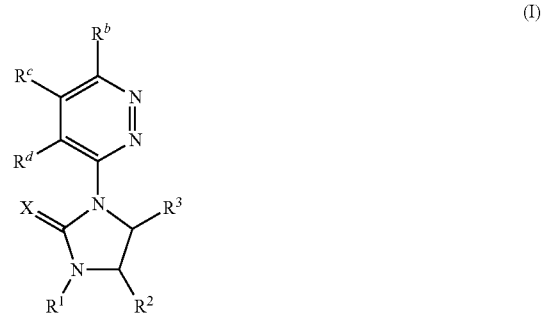

13 Claims, No Drawings

1-(PYRIDAZIN-3-YL)-IMIDAZOLIDIN-2-ONE DERIVATIVES AS HERBICIDES

RELATED APPLICATION INFORMATION

This application is a national stage entry of 371 of International Application No. PCT/EP2014/073943, filed Nov. 6, 2014, which claims priority to Indian Application Number IN/3309/DEL/2013, filed Nov. 11, 2013, the contents of which are incorporated herein by reference herein.

The present invention relates to certain substituted dihydro-hydantoin derivatives, to processes for their preparation, herbicidal compositions comprising them, and their use in controlling plants or inhibiting plant growth.

Herbicidal dihydro-hydantoins of the formula

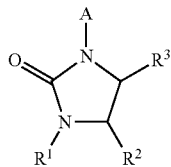

wherein A is a pyridazine ring are taught in U.S. Pat. No. 4,604,127. Similar compounds wherein A is a pyridine ring are taught in U.S. Pat. No. 4,600,430.

SUMMARY OF THE INVENTION

In a first aspect, the invention provides compounds of the formula (I)

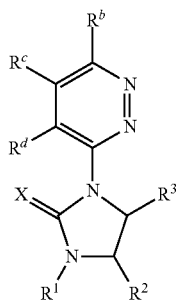

(I)

wherein
X is selected from S and O;
$R^b$ is selected from hydrogen, halogen, $C_1$-$C_4$ alkyl, $C_2$-$C_4$ alkenyl, $C_1$-$C_4$ haloalkyl, $C_1$-$C_6$ alkoxy, $C_2$-$C_4$ alkenyloxy, $C_2$-$C_4$ alkynyloxy, $C_1$-$C_4$ alkoxy-$C_1$-$C_4$ alkyl, $C_1$-$C_4$ halolkoxy, $C_1$-$C_3$ alkoxy-$C_1$-$C_3$ alkoxy, $C_1$-$C_4$-alkylthio, $C_1$-$C_4$ alkylsulfinyl, $C_1$-$C_4$ alkylsulfonyl, a group $R^5R^6N$—, a group $R^5C(O)N(R^6)$—, a group $R^5S(O_2)N(R^6)$—, a group $R^5R^6NSO_2$—, a group $R^5R^6NC(O)$—, aryl optionally substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, aryloxy optionally substituted by one of more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy and heteroaryl optionally substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;

$R^c$ is selected from $C_1$-$C_6$ haloalkyl and, when $R^b$ is $R^5R^6NC(O)$—, $R^c$ is selected from hydrogen, halogen, $C_1$-$C_4$ alkyl and $C_1$-$C_4$ haloalkyl;
$R^d$ is selected from hydrogen, halogen, cyano, $C_1$-$C_6$ alkyl and $C_1$-$C_6$ haloalkyl;
or $R^c$ and $R^d$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;
$R^1$ is selected from hydrogen, hydroxyl, $C_1$-$C_6$ alkyl optionally substituted with $NR^{10}R^{11}$, $C_2$-$C_6$ alkenyl, $C_2$-$C_6$ alkynyl, $C_1$-$C_4$ cycloalkyl, $C_1$-$C_4$ cyanoalkyl, $C_1$-$C_3$ haloalkyl, $C_1$-$C_6$ alkoxy and $C_1$-$C_4$ alkoxy-$C_1$-$C_4$ alkyl; wherein $R^{10}$ and $R^{11}$ are independently selected from hydrogen, $C_1$-$C_6$ alkyl and $C_1$-$C_6$ haloalkyl;
$R^2$ is selected from hydrogen, hydroxyl, halogen, $C_1$-$C_6$ alkyl, $C_2$-$C_6$ alkenyl, $C_2$-$C_6$ alkynyl, $C_1$-$C_6$ alkoxy, $C_2$-$C_6$ alkenyloxy, $C_2$-$C_6$ alkynyloxy, $C_1$-$C_6$ haloalkyl, $C_1$-$C_6$ haloalkoxy, $C_1$-$C_6$ alkoxy $C_1$-$C_6$ alkyl, $C_1$-$C_4$ alkoxy-$C_1$-$C_4$ alkoxy, $C_1$-$C_4$ hydroxyalkyl, $C_1$-$C_6$ cyanoalkyl and the group —$NR^{12}R^{13}$, wherein $R^{12}$ and $R^{13}$ are independently selected from hydrogen and $C_1$-$C_6$ alkyl;
or $R^1$ and $R^2$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from hydroxyl, =O, $C_1$-$C_6$ alkyl and $C_1$-$C_6$ haloalkyl;
$R^3$ is selected from halogen, hydroxyl, —$NR^{14}R^{15}$, and any one of the following groups

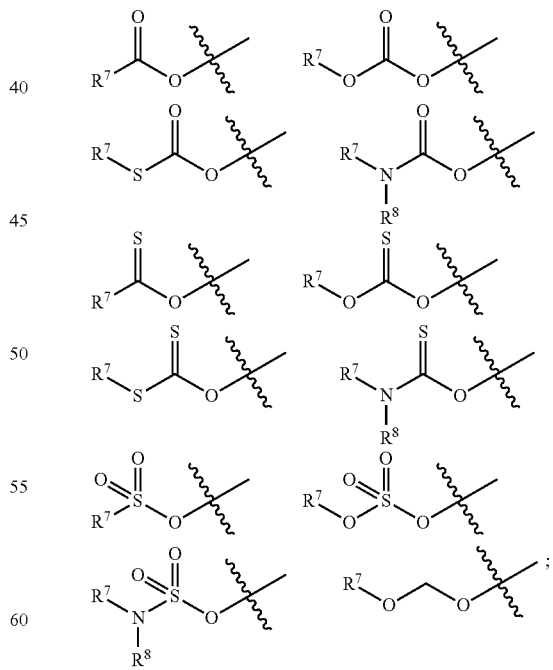

$R^5$ and $R^6$ are independently selected from hydrogen, $C_1$-$C_6$ alkyl, $C_1$-$C_6$ haloalkyl, $C_1$-$C_6$ cyanoalkyl, $C_2$-$C_6$ alkenyl, $C_2$-$C_6$ alkynyl, $C_1$-$C_6$ alkoxy and $C_1$-$C_6$ alkoxy-$C_1$-$C_6$ alkyl or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_3$-$C_6$ cycloalkyl group optionally substituted with 1 to 3 groups independently selected from $C_1$-$C_3$ alkyl, $C_2$-$C_4$ alkenyl, $C_1$-$C_3$ haloalkyl and $C_2$-$C_4$ haloalkenyl, a $C_5$-$C_{10}$ heterocyclyl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ arylalkyl group optionally substituted with 1 to 3 groups independently selected from $C_1$-$C_4$ alkyl, $C_1$-$C_3$ alkoxy, $C_1$-$C_3$ haloalkyl and the group —OC(O)—$C_1$-$C_4$ alkyl, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

$R^9$ is selected from $C_1$-$C_6$ alkyl and benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;

$R^{14}$ and $R^{15}$ are, independently, selected from hydrogen, $C_1$-$C_{20}$ alkyl, $C_1$-$C_{20}$ haloalkyl, $C_1$-$C_{20}$ alkoxy, $C_1$-$C_{20}$ alkoxy-$C_1$-$C_{20}$ alkyl, $C_2$-$C_{20}$ alkenyl, $C_2$-$C_{20}$ alkynyl and benzyl, or $R^{14}$ and $R^{15}$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

or an N-oxide or salt form thereof.

In a second aspect, the invention provides herbicidal compositions comprising a compound of the invention together with at least one agriculturally acceptable adjuvant or diluent.

In a third aspect, the invention provides the use of a compound or a composition of the invention for use as a herbicide.

In a fourth aspect, the invention provides a method of controlling weeds in crops of useful plants, comprising applying to said weeds or to the locus of said weeds, or to said useful crop plants, a compound or a composition of the invention.

In a fifth aspect, the invention relates to processes useful in the preparation of compounds of the invention.

In a sixth aspect, the invention relates to intermediates useful in the preparation of compounds of the invention.

DETAILED DESCRIPTION

In particularly preferred embodiments of the invention, the preferred groups for X, $R^b$, $R^c$, $R^d$, $R^1$, $R^2$ and $R^3$, in any combination thereof, are as set out below.

Preferably, X is O.

Preferably, $R^b$ is selected from hydrogen, halogen, $C_1$-$C_6$ alkoxy, a group $R^5R^6N$—, a group $R^5C(O)N(R^6)$—, a group $R^5S(O_2)N(R^6)$—, a group $R^5R^6NSO_2$—, a group $R^5R^6NC(O)$—, aryl optionally substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, and heteroaryl optionally substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

More preferably, $R^b$ is selected from hydrogen, halogen, methoxy, $R^5R^6NC(O)$—, heteroaryl substituted by halogen or methoxy groups and aryl substituted by halogen or methoxy groups.

Even more preferably, $R^b$ is selected from hydrogen and halogen.

Preferably, $R^c$ is selected from 1,1-difluoroethyl, difluoromethyl, 1-fluoro-1-methylethyl and trifluoromethyl, or, when $R^b$ is $R^5R^6NC(O)$—, $R^c$ is selected from hydrogen, Cl and trifluoromethyl.

More preferably, $R^c$ is selected from 1,1-difluoroethyl, 1-fluoro-1-methylethyl and trifluoromethyl.

Most preferably, $R^c$ is trifluoromethyl.

Preferably, $R^d$ is hydrogen.

Preferably $R^1$ is selected from hydrogen, $C_1$-$C_6$ alkyl optionally substituted with $NR^{10}R^{11}$, $C_1$-$C_3$ haloalkyl and $C_1$-$C_6$ alkoxy; wherein $R^{10}$ and $R^{11}$ are independently selected from hydrogen, $C_1$-$C_6$ alkyl and $C_1$-$C_6$ haloalkyl.

More preferably, $R^1$ is selected from $C_1$-$C_3$ alkyl, $C_1$-$C_3$ alkoxy and $C_1$-$C_3$ haloalkyl.

Even more preferably $R^1$ is selected from methyl and methoxy.

Preferably, $R^2$ is selected from hydrogen, hydroxyl, halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ alkoxy $C_1$-$C_6$ alkyl, $C_1$-$C_6$ cyanoalkyl and the group —$NR^{12}R^{13}$, wherein $R^{12}$ and $R^{13}$ are independently selected from hydrogen and $C_1$-$C_6$ alkyl.

More preferably, $R^2$ is selected from hydrogen, hydroxyl, $C_1$-$C_3$ alkyl, $C_1$-$C_3$ alkoxy, $C_1$-$C_3$ haloalkyl and $C_1$-$C_3$ alkoxy-$C_1$-$C_3$ alkyl.

Even more preferably $R^2$ is selected from hydrogen, methyl, methoxy, ethoxy and methoxymethyl.

Preferably, $R^3$ is selected from halogen, hydroxyl, and any one of the following groups

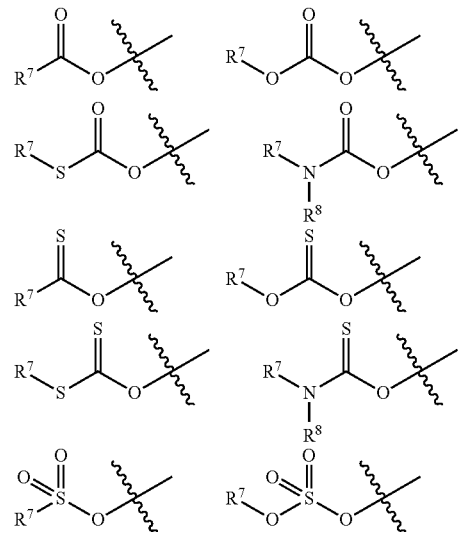

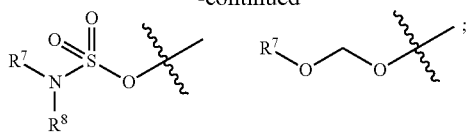

More preferably, $R^3$ is selected from halogen, hydroxyl, or any of the following groups

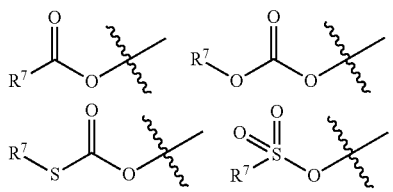

Even more preferably, $R^3$ is selected from hydroxyl, halogen, $C_1$-$C_6$ alkylcarbonyloxy, $C_1$-$C_6$ alkoxycarbonyloxy and aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

Even more preferably, $R^3$ is selected from hydroxyl and halogen.

Most preferably, $R^3$ is hydroxyl.

Preferably, $R^5$ and $R^6$ are independently selected from hydrogen, $C_1$-$C_6$ alkyl, $C_1$-$C_6$ haloalkyl, $C_2$-$C_6$ alkenyl, $C_2$-$C_6$ alkynyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl.

Preferably, $R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_3$-$C_6$ cycloalkyl group optionally substituted with 1 to 3 groups independently selected from $C_1$-$C_3$ alkyl, $C_2$-$C_4$ alkenyl, $C_1$-$C_3$ haloalkyl and $C_2$-$C_4$ haloalkenyl, a $C_5$-$C_{10}$ heterocyclyl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ arylalkyl group optionally substituted with 1 to 3 groups independently selected from $C_1$-$C_4$ alkyl, $C_1$-$C_3$ alkoxy, $C_1$-$C_3$ haloalkyl and the group —OC(O)—$C_1$-$C_4$ alkyl, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl.

More preferably, $R^7$ is selected from $C_1$-$C_6$ alkyl, $C_1$-$C_6$ haloalkyl, $C_2$-$C_6$ alkenyl, $C_2$-$C_6$ alkynyl, a $C_5$-$C_{10}$ monocyclic heteroaryl group comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

The compounds of formula (I) may exist as different geometric isomers, or in different tautomeric forms. This invention covers all such isomers and tautomers, and mixtures thereof in all proportions, as well as isotopic forms such as deuterated compounds.

The compounds of this invention may contain one or more asymmetric centers and may thus give rise to optical isomers and diastereomers. While shown without respect to stereochemistry, the present invention includes all such optical isomers and diastereomers as well as the racemic and resolved, enantiomerically pure R and S stereoisomers and other mixtures of the R and S stereoisomers and agrochemically acceptable salts thereof. It is recognized certain optical isomers or diastereomers may have favorable properties over the other. Thus when disclosing and claiming the invention, when a racemic mixture is disclosed, it is clearly contemplated that both optical isomers, including diastereomers, substantially free of the other, are disclosed and claimed as well.

Alkyl, as used herein, refers to an aliphatic hydrocarbon chain and includes straight and branched chains e. g. of 1 to 8 carbon atoms such as methyl, ethyl, n-propyl, isopropyl, n-butyl, isobutyl, sec-butyl, t-butyl, n-pentyl, isopentyl, neo-pentyl, n-hexyl, and isohexyl.

Alkenyl, as used herein, refers to an aliphatic hydrocarbon chain having at least one double bond, and preferably one double bond, and includes straight and branched chains e. g. of 2 to 8 carbon atoms such as ethenyl (vinyl), prop-1-enyl, prop-2-enyl (allyl), isopropenyl, but-1-enyl, but-2-enyl, but-3-enyl, 2-methypropenyl.

Alkynyl, as used herein, refers to an aliphatic hydrocarbon chain having at least one triple bond, and preferably one triple bond, and includes straight and branched chains e. g. of 2 to 8 carbon atoms such as ethynyl, prop-1-ynyl, prop-2-ynyl (propargyl) but-1-ynyl, but-2-ynyl and but-3-ynyl.

Cycloalkyl, as used herein, refers to a cyclic, saturated hydrocarbon group having from 3 to 6 ring carbon atoms. Examples of cycloalkyl groups are cyclopropyl, cyclobutyl, cyclopentyl and cyclohexyl.

Hydroxyalkyl, as used herein, refers to the group —ROH, wherein R is alkyl as defined above.

Alkoxy, as used herein, refers to the group —OR, wherein R is alkyl as defined above.

Examples of alkoxy groups include methoxy, ethoxy, n-propoxy, isopropoxy, n-butoxy, isobutoxy, sec-butoxy, t-butoxy, n-pentoxy, isopentoxy, neo-pentoxy, n-hexyloxy, and isohexyloxy.

Alkoxyalkyl, as used herein, refers to the group —ROR, wherein each R is, independently, an alkyl group as defined above.

Alkoxyalkoxy, as used herein, refers to the group —OROR, wherein each R is, independently, an alkyl group as defined above.

Alkenyloxy, as used herein, refers to the group —OR, wherein R is alkenyl as used herein. Examples of alkenyloxy groups are ethenyloxy, propenyloxy, isopropenyloxy, but-1-enyloxy, but-2-enyloxy, but-3-enyloxy, 2-methypropenyloxy etc.

Alkynyloxy, as used herein, refers to the group —OR, wherein R is alkynyl as used herein. Examples of alkynyloxy groups are ethynyloxy, propynyloxy, but-1-ynyloxy, but-2-ynyloxy and but-3-ynyloxy.

Cyanoalkyl, as used herein, refers to an alkyl group substituted with one or more cyano groups.

Halogen, halide and halo, as used herein, refer to iodine, bromine, chlorine and fluorine.

Haloalkyl, as used herein, refers to an alkyl group as defined above wherein at least one hydrogen atom has been replaced with a halogen atom as defined above. Examples of haloalkyl groups include chloromethyl, dichloromethyl, trichloromethyl, fluoromethyl, difluoromethyl and trifluoromethyl. Preferred haloalkyl groups are fluoroalkyl groups {i.e. haloalkyl groups, containing fluorine as the only halogen). More highly preferred haloalkyl groups are perfluoroalkyl groups, i.e. alkyl groups wherein all the hydrogen atoms are replaced with fluorine atoms.

Haloalkoxy, as used herein, refers to the group —OR, wherein R is haloalkyl as defined above.

Alkylthio, as used herein, refers to the group —SR, wherein R is an alkyl group as defined above. Alkylthio groups include, but are not limited to, methylthio, ethylthio, propylthio, tert-butylthio, and the like.

Alkylsulfinyl, as used herein, refers to the group —S(O)R, wherein R is an alkyl group as defined above.

Alkylsulfonyl, as used herein, refers to the group —S(O)$_2$R, wherein R is an alkyl group as defined above.

Alkycarbonyloxy, as used herein, refers to the group —OC(O)R, wherein R is an alkyl group as defined above.

Alkoxycarbonyloxy, as used herein, refers to the group —OC(O)OR, wherein R is an alkyl group as defined above. Examples of alkoxycarbonyloxy groups are methoxycarbonyloxy, ethoxycarbonyloxy, propoxycarbonyloxy, but-1-oxycarbonyloxy, but-2-oxycarbonyloxy and but-3-oxycarbonyloxy.

Hydroxy or hydroxyl, as used herein, refers to the group —OH.

Nitro, as used herein, refers to the group —NO$_2$.

Cyano as used herein, refers to the group —CN.

Aryl, as used herein, refers to an unsaturated aromatic carbocyclic group of from 6 to 10 carbon atoms having a single ring (e. g., phenyl) or multiple condensed (fused) rings, at least one of which is aromatic (e.g., indanyl, naphthyl). Preferred aryl groups include phenyl, naphthyl and the like. Most preferably, an aryl group is a phenyl group.

Aryloxy, as used herein, refers to the group —O-aryl, wherein aryl is as defined above.

Preferred aryloxy groups include phenoxy, naphthyloxy and the like.

Aryloxycarbonyloxy, as used herein, refers to the group —OC(O)O-aryl wherein aryl is a as defined above.

Arylalkyl, as used herein, refers to a group R—Ar, wherein R is alkyl as defined herein and Ar is aryl as defined herein. Arylalkyl groups may be substituted on the alkyl linker or on the ring. An example of an arylalkyl group is the benzyl group (—CH$_2$C$_6$H$_5$).

Heterocyclyl, as used herein, refers to a non-aromatic ring system containing 3 to 10 ring atoms, at least one ring heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyrrolidinyl, imidazolinyl, pyrazolidinyl, piperidyl, piperazinyl, quinuclidinyl, morpholinyl, together with unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Heteroaryl, as used herein, refers to a ring system containing 5 to 10 ring atoms, 1 to 4 ring heteroatoms and consisting either of a single aromatic ring or of two or more fused rings, at least one of which is aromatic. Preferably, single rings will contain up to three and bicyclic systems up to four heteroatoms which will preferably be independently chosen from nitrogen, oxygen and sulfur. Examples of such groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. Examples of bicyclic groups are benzothiophenyl, benzimidazolyl, benzothiadiazolyl, quinolinyl, cinnolinyl, quinoxalinyl and pyrazolo[1,5-a]pyrimidinyl.

'Saturated ring', as used herein, refers to a ring system in which the atoms in the ring are linked by single bonds.

'Partially unsaturated ring', as used herein, refers to a ring system in which at least two atoms in the ring are linked by a double bond. Partially unsaturated ring systems do not include aromatic rings.

"Optionally substituted" as used herein means the group referred to can be substituted at one or more positions by any one or any combination of the radicals listed thereafter. For most groups, one or more hydrogen atoms are replaced by the radicals listed thereafter. For halogenated groups, for example, haloalkyl groups, one or more halogen atoms are replaced by the radicals listed thereafter.

Suitable salts include those derived from alkali or alkaline earth metals and those derived from ammonia and amines. Preferred cations include sodium, potassium, magnesium, and ammonium cations of the formula N$^+$(R$^{19}$R$^{20}$R$^{21}$R$^{22}$) wherein R$^{19}$, R$^{20}$, R$^{21}$ and R$^{22}$ are independently selected from hydrogen, C$_1$-C$_6$ alkyl and C$_1$-C$_6$ hydroxyalkyl. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

In another aspect the present invention provides intermediates useful in the preparation of compounds of the invention.

In one embodiment, there are provided intermediates of the formula (III) wherein R$^1$, R$^2$, R$^b$, R$^c$ and R$^d$ are as defined above.

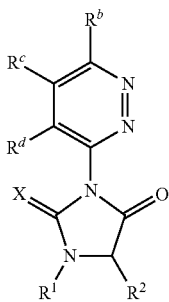

In another embodiment, there are provided intermediates shown below wherein X, $R^1$, $R^2$, $R^{14}$, $R^{15}$, $R^a$, $R^b$, $R^c$ and $R^d$ are as defined above.

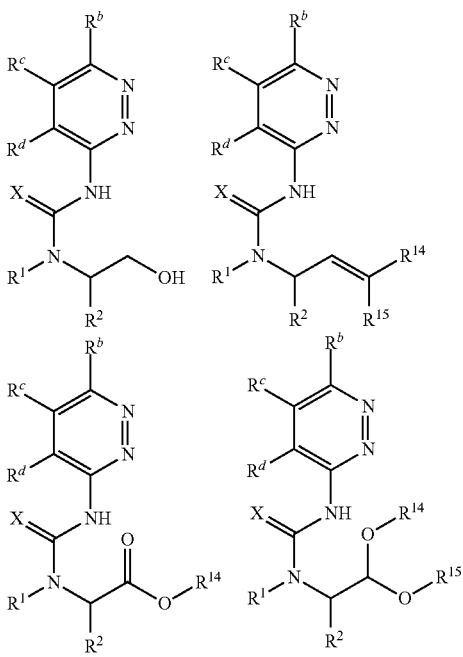

Compounds of the invention may be prepared by techniques known to the person skilled in the art of organic chemistry. General methods for the production of compounds of formula (I) are described below. Unless otherwise stated in the text, the substituents $R^1$, $R^2$, $R^3$, Rb, $R^c$ and $R^d$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

For example, compounds of formula (IX) wherein $R^1$ is an alkyl or alkoxy group and $R^2$ is a hydrogen or alkyl group may be prepared by reaction of amino-pyridazine (IV) with phenylchloroformate to give carbamate product (V). The subsequent reaction with an appropriately substituted amino-ester (VI) gives compounds of type (VII) and subsequent cyclisation gives compounds of type (VIII) and reduction with e.g. with sodium borohydride gives compounds of type (IX). The methyl amino-ester (VI) may also be replaced by other amino esters or amino-acids. Phenyl chloroformate may be replaced by other activating groups such as phosgene or para-nitrophenyl chlorofomate. The cyclisation to (VIII) may occur in situ or require heating for carboxylic acids or esters or treatment with a reagent such as thionyl chloride for carboxylic acids. Esters of type (VII) may also be reduced to their corresponding primary alcohols and then such alcohols can be re-oxidised to compounds of type (IX) with oxidants such as Dess-Martin periodinane.

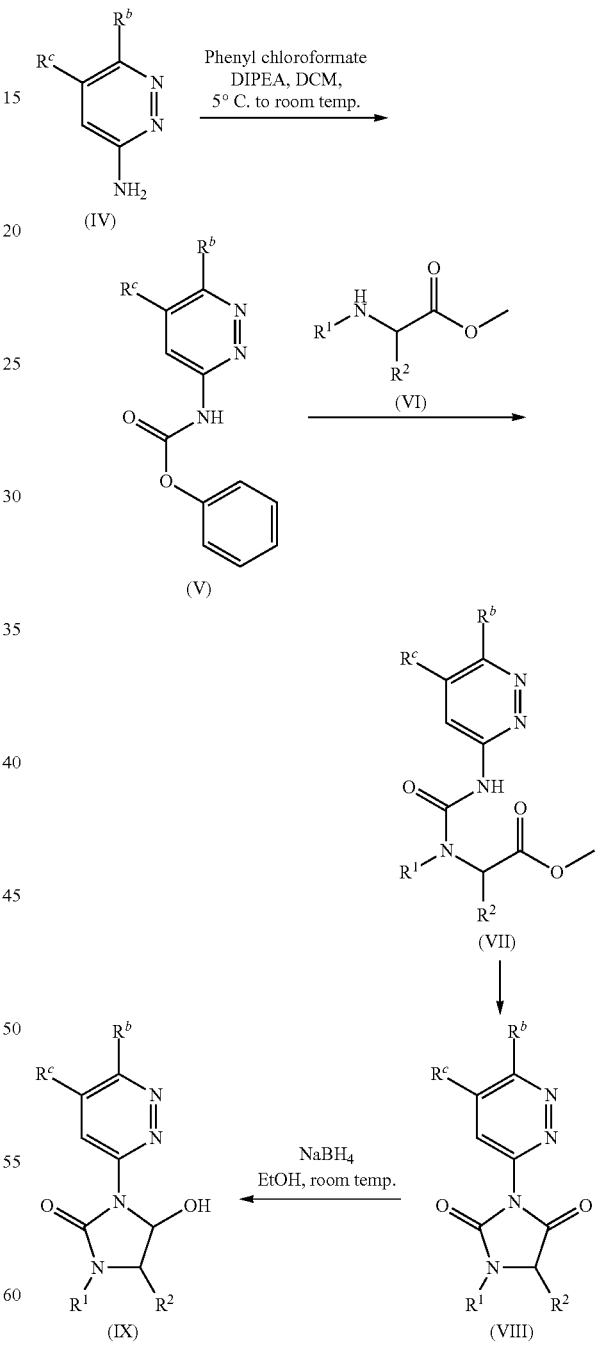

Alternatively, compounds of formula (IX) wherein $R^1$ is an alkyl group or alkoxy group and $R^2$ is a hydrogen or alkyl group may be prepared by Palladium catalysed reaction of chloro-pyridazine (X) with urea (XI) to give (XII) (for a reference to a related reaction see WO2006048249, example 3.1) and then subsequent cyclisation gives compounds of type (IX).

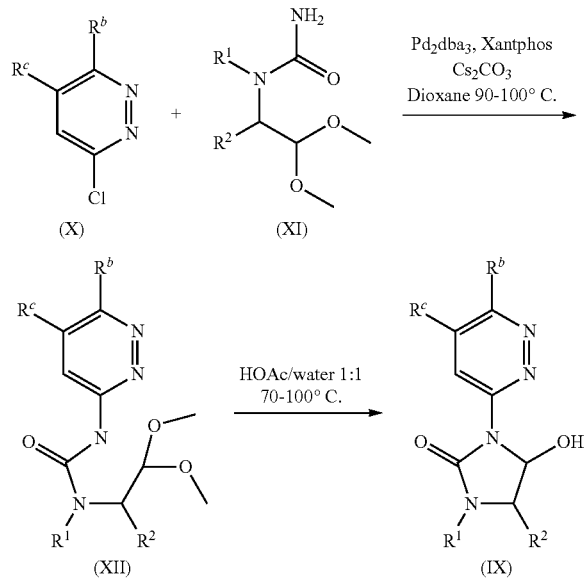

Urea (XI) may be formed by reaction of ester (XIII) with Grignard reagents, reductive amination of the product ketone (XIV) with amines and finally reaction of the subsequent product amine (XV) with TMS-isocyanate to give compounds of type (XI). Alternatively (XV) can be formed by a Grignard addition of type $R_2MgCl$ to appropriate imines. Alternatively, a nitrile can replace the ester group of (XIII) in the reaction with Grignard reagents.

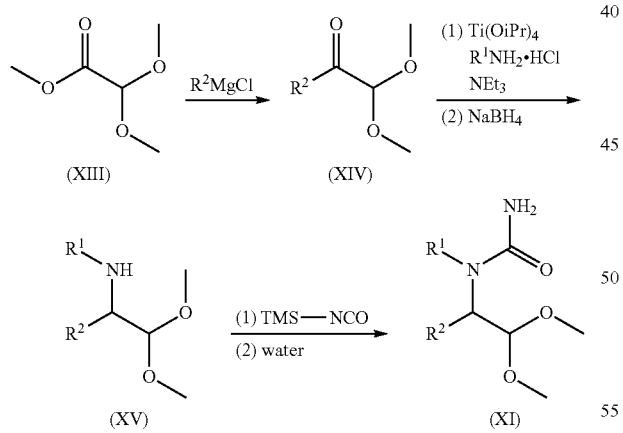

Alternatively, reaction of compounds of type (XIV) with methoxylamine following by reduction of the oxime ether formed gives compounds of type (XV) which can form compounds of type (XI) where R1 is alkoxy. Alternatively, reaction of compounds of type (XIV) where R2 is hydrogen with methoxylamine follow by addition of Grignard reagents to the formed oxime also can give compounds of type (XV).

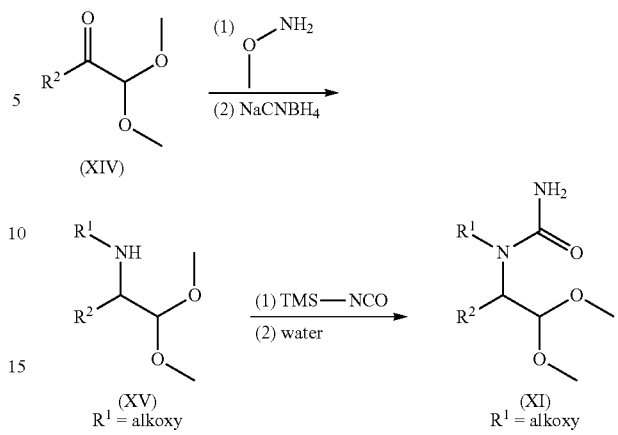

Compounds of formula (XVIII) wherein $R^2$ is an hydroxy group may be prepared by the Palladium catalysed reaction of chloro-pyridazine (X) with urea (XVI) to give urea (XVII) (for a reference to a related reaction see WO2006048249, example 3.1), which can react with aqueous glyoxal solution to give product (XVIII). Compounds of formula (IX) where $R_2$ is an alkoxy group may be prepared by reacting compounds of formula (XVIII) with alcohols of type $R_4$—OH under acidic conditions.

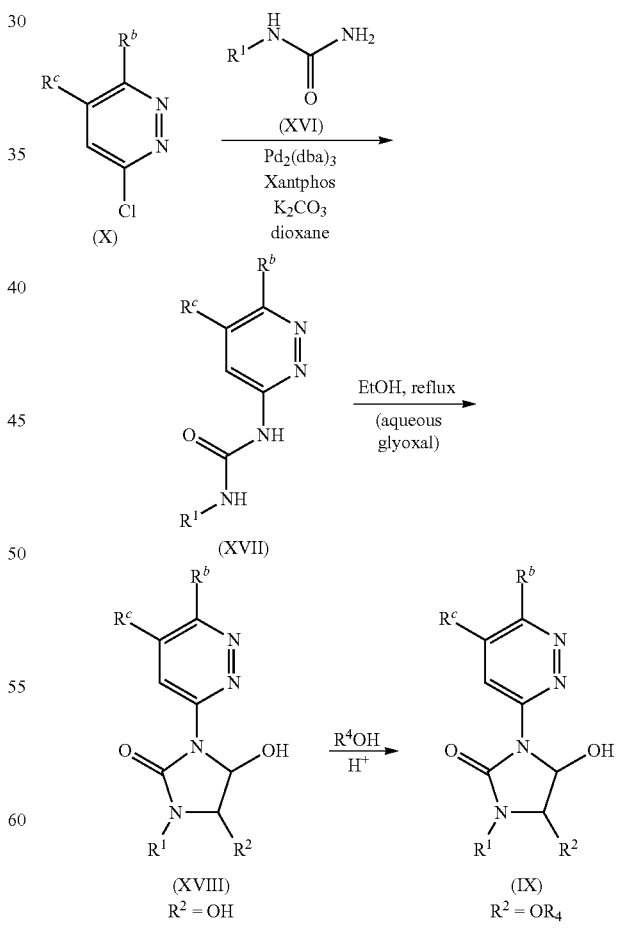

Alternatively, compounds of formula (V) may be reacted with compounds of formula (XIX) wherein $R^2$ is a hydrogen or alkyl group to give products of type (XX). Cyclisation with a suitable reagent such as thionyl chloride gives compounds of formula (XXI), which can be alkylated with a suitable base such as LiHMDS and a suitable alkylating agent such as methyl iodide (for $R_1$=Me) to give compound (VIII). Reduction as before gives compounds of type (IX).

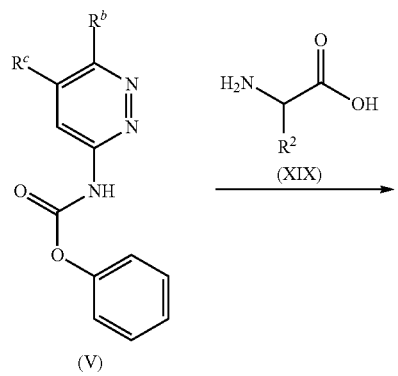

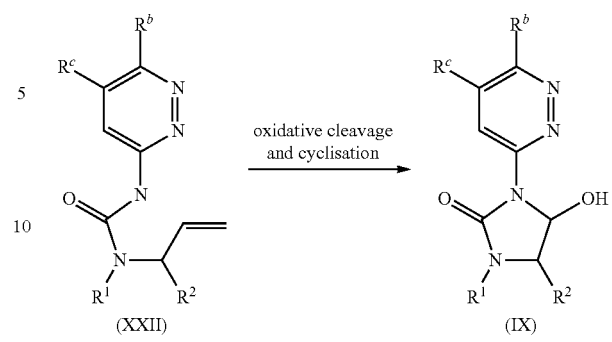

Alternatively, compounds of type (XXIII) may be coupled with compounds of type (X) under Palladium catalysed conditions to give compounds of type (VIII) and then standard reduction with $NaBH_4$ for example gives products of type (IX).

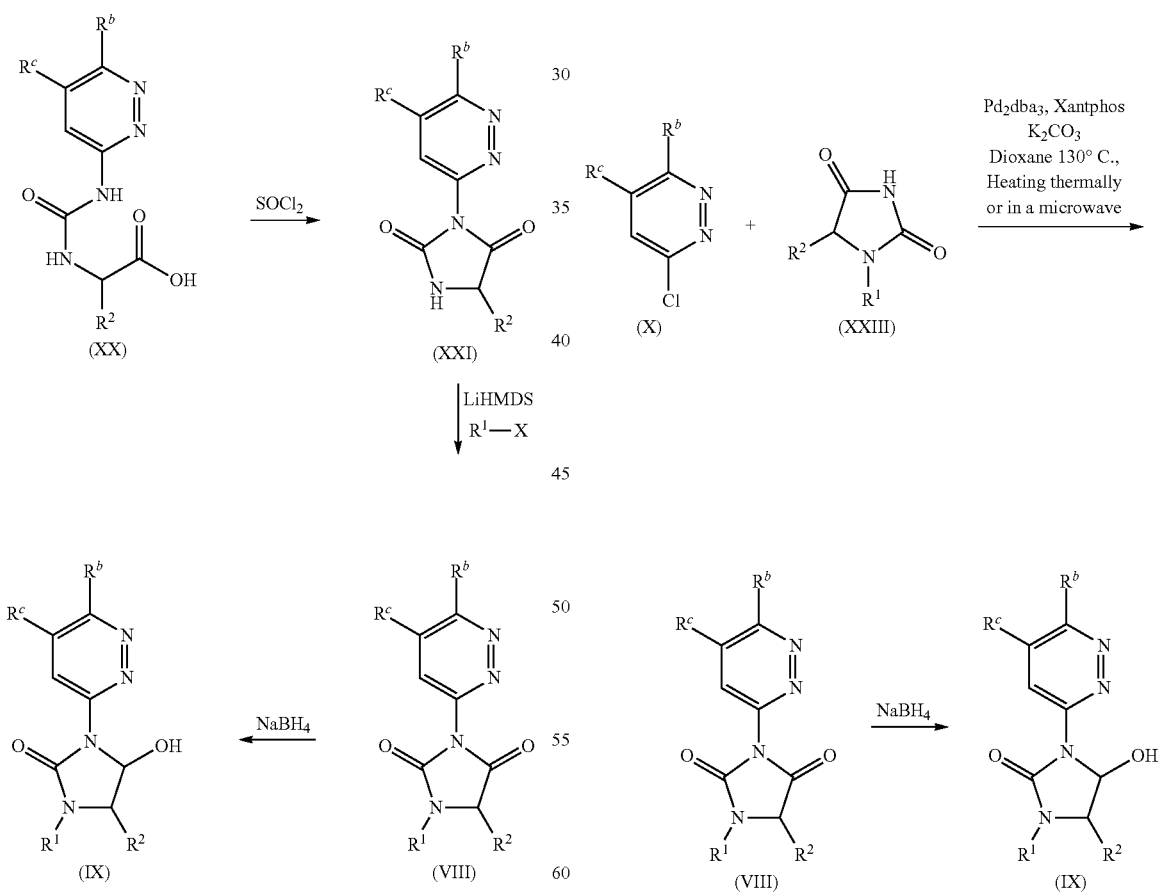

Alternatively oxidative cleavage (using ozonolysis or $OsO_4/NaIO_4$ or similar conditions) of an appropriate vinyl compound such as (XXII) or derivatives thereof and cyclisation could give the desired product.

Amino and chloro-pyridazines may be made by standard procedures such as those outlined below.

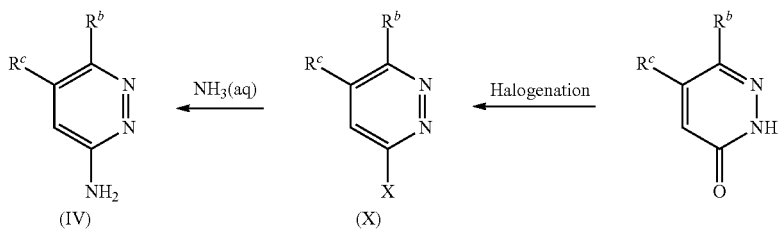

Chloro-pyridazines may be also made by standard procedures such as those outlined below from hydrazine and maleic anhydrides.

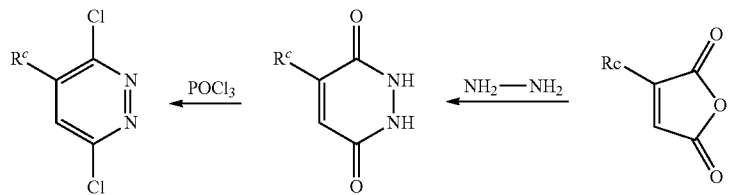

Substituted chloro-pyridazines may be obtained using Minisci type chemistry—for a review see *Med. Chem. Commun.*, 2011, 2, 1135 or via alternative radical conditions—see *Nature*, 2012, 492, 95, and *Angew. Chem. Int. Ed.*, 2013, 52, 3949.

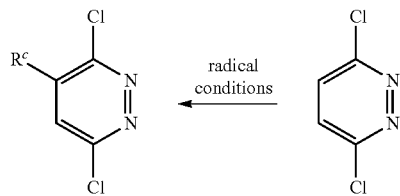

Suitable conditions for effecting these transformations are set out in texts such as J. March, Advanced Organic Chemistry, 4th ed. Wiley, New York, 1992.

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. Therefore, the invention also relates to a herbicidal composition which comprises a herbicidally effective amount of a compound of formula (I) in addition to formulation adjuvants. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilizers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydro-furfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery®2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltrilosanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-Trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%

Dusts:
active ingredient: 0.1 to 10%, preferably 0.1 to 5%
solid carrier: 99.9 to 90%, preferably 99.9 to 99%

Suspension Concentrates:
active ingredient: 5 to 75%, preferably 10 to 50%
water: 94 to 24%, preferably 88 to 30%
surface-active agent: 1 to 40%, preferably 2 to 30%

Wettable Powders:
active ingredient: 0.5 to 90%, preferably 1 to 80%
surface-active agent: 0.5 to 20%, preferably 1 to 15%
solid carrier: 5 to 95%, preferably 15 to 90%

Granules:
active ingredient: 0.1 to 30%, preferably 0.1 to 15%
solid carrier: 99.5 to 70%, preferably 97 to 85%

The following Examples further illustrate, but do not limit, the invention.

Formulation Examples for Herbicides of Formula (I) (%=% by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention also provides a method of controlling plants which comprises applying to the plants or to the locus thereof a herbicidally effective amount of a compound of formula (I).

The invention also provides a method of inhibiting plant growth which comprises applying to the plants or to the locus thereof a herbicidally effective amount of a compound of formula (I).

The invention also provides a method of controlling weeds in crops of useful plants, comprising applying to said weeds or to the locus of said weeds, or to said useful plants or to the locus of said useful plants, a compound or a composition of the invention.

The invention also provides a method of selectively controlling grasses and/or weeds in crops of useful plants which comprises applying to the useful plants or locus thereof or to the area of cultivation a herbicidally effective amount of a compound of formula (I).

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like.

The term "plants" refers to all physical parts of a plant, including seeds, seedlings, saplings, roots, tubers, stems, stalks, foliage, and fruits. The term "locus" is intended to include soil, seeds, and seedlings, as well as established vegetation and includes not only areas where weeds may already be growing, but also areas where weeds have yet to emerge, and also to areas under cultivation with respect to crops of useful plants. "Areas under cultivation" include land on which the crop plants are already growing and land intended for cultivation with such crop plants. The term "weeds" as used herein means any undesired plant, and thus includes not only agronomically important weeds as described below, but also volunteer crop plants.

The compounds of the invention can be applied before or after planting of the crops, before weeds emerge (pre-emergence application) or after weeds emerge (post-emergence application), and are particularly effective when applied post-emergence to the weeds.

Crops of useful plants in which the composition according to the invention can be used include, but are not limited to, perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals, switchgrass, turf and vegetables, especially cereals, maize and soy beans.

The grasses and weeds to be controlled may be both monocotyledonous species, for example *Agrostis, Alopecurus, Avena, Brachiaria, Bromus, Cenchrus, Cyperus, Digitaria, Echinochloa, Eriochloa, Lolium, Monochoria, Panicum, Poa, Rottboellia, Sagittaria, Scirpus, Setaria, Sida* and *Sorghum*, and dicotyledonous species, for example *Abutilon, Amaranthus, Chenopodium, Chrysanthemum, Euphorbia, Galium, Ipomoea, Kochia, Nasturtium, Polygonum, Sida, Sinapis, Solanum, Stellaria, Veronica, Viola* and *Xanthium*.

In all aspects of the invention, in a particular embodiment, the weeds, e.g. to be controlled and/or growth-inhibited may be monocotyledonous or dicotyledonous weeds, which are tolerant or resistant to one or more other herbicides for example, HPPD inhibitor herbicides such as mesotrione, PSII inhibitor herbicides such as atrazine or EPSPS inhibitors such as glyphosate. Such weeds include, but are not limited to resistant *Amaranthus* biotypes.

Crops are to be understood as also including those crops which have been rendered tolerant to herbicides or classes of herbicides (e.g. auxins or ALS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, respectively.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Any method of application to weeds/crop of useful plant, or locus thereof, which is routinely used in agriculture may be used, for example application by spray or broadcast method typically after suitable dilution of a compound of formula (I) (whether said compound is formulated and/or in combination with one or more further active ingredients and/or safeners, as described herein).

The compounds of formula (I) according to the invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth, form yet further aspects of the invention. For the avoidance of doubt, mixtures of invention also include mixtures of two or more different compounds of formula (I). In particular, the present invention also relates to a composition of the invention which comprises at least one further herbicide in addition to the compound of formula (I).

When a compound of formula (I) is combined with at least one additional herbicide, the following mixtures of the compound of formula (I) are preferred. Compound of formula (I)+acetochlor, compound of formula (I)+acifluorfen, compound of formula (I)+acifluorfen-sodium, compound of formula (I)+aclonifen, compound of formula (I)+acrolein, compound of formula (I)+alachlor, compound of formula (I)+alloxydim, compound of formula (I)+allyl alcohol, compound of formula (I)+ametryn, compound of formula (I)+amicarbazone, compound of formula (I)+amidosulfuron, compound of formula (I)+aminocyclopyrachlor, compound of formula (I)+aminopyralid, compound of formula (I)+amitrole, compound of formula (I)+ammonium sulfamate, compound of formula (I)+anilofos, compound of formula (I)+asulam, compound of formula (I)+atrazine, formula (I)+aviglycine, formula (I)+azafenidin, compound of formula (I)+azimsulfuron, compound of formula (I)+BCPC, compound of formula (I)+beflubutamid, compound of formula (I)+benazolin, formula (I)+bencarbazone, compound of formula (I)+benfluralin, compound of formula (I)+benfuresate, compound of formula (I)+bensulfuron, compound of formula (I)+bensulfuron-methyl, compound of formula (I)+bensulide, compound of formula (I)+bentazone, compound of formula (I)+benzfendizone, compound of formula (I)+benzobicyclon, compound of formula (I)+benzofenap, compound of formula (I)+bicyclopyrone, compound of formula (I)+bifenox, compound of formula (I)+bilanafos, compound of formula (I)+bispyribac, compound of formula (I)+bispyribac-sodium, compound of formula (I)+borax, compound of formula (I)+bromacil, compound of formula (I)+bromobutide, formula (I)+bromophenoxim, compound of formula (I)+bromoxynil, compound of formula (I)+butachlor, compound of formula (I)+butafenacil, compound of formula (I)+butamifos, compound of formula (I)+butralin, compound of formula (I)+butroxydim, compound of formula (I)+butylate, compound of formula (I)+cacodylic acid, compound of formula (I)+calcium chlorate, compound of formula (I)+cafenstrole, compound of formula (I)+carbetamide, compound of formula (I)+carfentrazone, compound of formula (I)+carfentrazone-ethyl, compound of formula (I)+CDEA, compound of formula (I)+CEPC, compound of formula (I)+chlorflurenol, compound of formula (I)+chlorflurenol-methyl, compound of formula (I)+chloridazon, compound of formula (I)+chlorimuron, compound of formula (I)+chlorimuron-ethyl, compound of formula (I)+chloroacetic acid, compound of formula (I)+chlorotoluron, compound of formula (I)+chlorpropham, compound of formula (I)+chlorsulfuron, compound of formula (I)+chlorthal, compound of formula (I)+chlorthal-dimethyl, compound of formula (I)+cinidon-ethyl, compound of formula (I)+cinmethylin, compound of formula (I)+cinosulfuron, compound of formula (I)+cisanilide, compound of formula (I)+clethodim, compound of formula (I)+clodinafop, compound of formula (I)+clodinafop-propargyl, compound of formula (I)+clomazone, compound of formula (I)+clomeprop, compound of formula (I)+clopyralid, compound of formula (I)+cloransulam, compound of formula (I)+cloransulam-methyl, compound of formula (I)+CMA, compound of formula (I)+4-CPB, compound of formula (I)+CPMF, compound of formula (I)+4-CPP, compound of formula (I)+CPPC, compound of formula (I)+cresol, compound of formula (I)+cumyluron, compound of formula (I)+cyanamide, compound of formula (I)+cyanazine, compound of formula (I)+cycloate, compound of formula (I)+cyclosulfamuron, compound of formula (I)+cycloxydim, compound of formula (I)+cyhalofop, compound of formula (I)+cyhalofop-butyl, compound of formula (I)+2,4-D, compound of formula (I)+3,4-DA, compound of formula (I)+daimuron, compound of formula (I)+dalapon, compound of formula (I)+dazomet, compound of formula (I)+2,4-DB, compound of formula (I)+3,4-DB, compound of formula (I)+2,4-DEB, compound of formula (I)+desmedipham, formula (I)+desmetryn, compound of formula (I)+dicamba, compound of formula (I)+dichlobenil, compound of formula (I)+ortho-dichlorobenzene, compound of formula (I)+para-dichlorobenzene, compound of formula (I)+dichlorprop, compound of formula (I)+dichlorprop-P, compound of formula (I)+diclofop, compound of formula (I)+diclofop-methyl, compound of formula (I)+diclosulam, compound of formula (I)+difenzoquat, compound of formula (I)+difenzoquat metilsulfate, compound of formula (I)+diflufenican, compound of formula (I)+diflufenzopyr, compound of formula (I)+dimefuron, compound of formula (I)+dimepiperate, compound of formula (I)+dimethachlor, compound of formula (I)+dimethametryn, compound of formula (I)+dimethenamid, compound of formula (I)+dimethenamid-P, compound of formula (I)+dimethipin, compound of formula (I)+dimethylarsinic acid, compound of formula (I)+dinitramine, compound of formula (I)+dinoterb, compound of formula (I)+diphenamid, formula (I)+dipropetryn, compound of formula (I)+diquat, compound of formula (I)+diquat dibromide, compound of formula (I)+dithiopyr, compound of formula (I)+diuron, compound of formula (I)+DNOC, compound of formula (I)+3,4-DP, compound of formula (I)+DSMA, compound of formula (I)+EBEP, compound of formula (I)+endothal, compound of formula (I)+EPTC, compound of formula (I)+esprocarb, compound of formula (I)+ethalfluralin, compound of formula (I)+ethametsulfuron, compound of formula (I)+ethametsulfuron-methyl, formula (I)+ethephon, compound of formula (I)+ethofumesate, compound of formula (I)+ethoxyfen, compound of formula (I)+ethoxysulfuron, compound of formula (I)+etobenzanid, compound of formual (I)+fenoxaprop, compound of formula (I)+fenoxaprop-P, compound of formula (I)+fenoxaprop-ethyl, compound of formula (I)+fenoxaprop-P-ethyl, compound of formula (I)+fentrazamide, compound of formula (I)+ferrous sulfate, compound of formula (I)+flamprop-M, compound of formula (I)+flazasulfuron, compound of formula (I)+florasulam, compound of formula (I)+fluazifop, compound of formula (I)+fluazifop-butyl, compound of formula (I)+fluazifop-P, compound of formula (I)+fluazifop-P-butyl, formula (I)+fluazolate, compound of formula (I)+flucarbazone, compound of formula (I)+flucarbazone-sodium, compound of formula (I)+flucetosulfuron, compound of formula (I)+fluchloralin, compound of formula (I)+flufenacet, compound of formula (I)+flufenpyr, compound of formula (I)+flufenpyr-ethyl, formula (I)+flumetralin, compound of formula (I)+flumetsulam, compound of formula (I)+flumiclorac, compound of formula (I)+flumiclorac-pentyl, compound of formula (I)+flumioxazin, formula (I)+flumipropin, compound of formula (I)+fluometuron, compound of formula (I)+fluoroglycofen, compound of formula (I)+fluoroglycofen-ethyl, formula (I)+fluoxaprop, formula (I)+flupoxam, formula (I)+flupropacil, compound of formula (I)+flupropanate, compound of formula (I)+flupyrsulfuron, compound of formula (I)+flupyrsulfuron-methyl-sodium, compound of formula (I)+flurenol, compound of formula (I)+fluridone, compound of formula (I)+flurochloridone, compound of formula (I)+fluroxypyr, compound of formula (I)+flurtamone, compound of formula (I)+fluthiacet, compound of formula (I)+fluthiacet-methyl, compound of formula (I)+fomesafen, compound of formula (I)+foramsulfuron, compound of formula (I)+fosamine, compound of formula (I)+glufosinate, compound of formula (I)+glufosinate-ammonium, compound of formula (I)+glyphosate, compound of formula (I)+halauxifen, compound of formula (I)+halauxifen-methyl, compound of formula (I)+halosulfuron, compound of formula (I)+halosulfuron-methyl, compound of formula (I)+haloxyfop, compound of formula (I)+haloxyfop-P, compound of formula (I)+HC-252, compound of formula (I)+hexazinone, compound of formula (I)+imazamethabenz, compound of formula (I)+imazamethabenz-methyl, compound of formula (I)+imazamox, compound of formula (I)+imazapic, compound of formula (I)+imazapyr, compound of formula (I)+imazaquin, compound of formula (I)+imazethapyr, compound of formula (I)+imazosulfuron, compound of formula (I)+indanofan, compound of formula (I) and indaziflam, compound of formula (I)+iodomethane, compound of formula (I)+iodosulfuron, compound of formula (I)+iodosulfuron-methyl-sodium, compound of formula (I)+ioxynil, compound of formula (I) and ipfencarbazone, compound of formula (I)+isoproturon, compound of formula (I)+isouron, compound of formula (I)+isoxaben, compound of formula (I)+isoxachlortole, compound of formula (I)+isoxaflutole, formula (I)+isoxapyrifop, compound of formula (I)+karbutilate, compound of formula (I)+lactofen, compound of formula (I)+lenacil, compound of formula (I)+linuron, compound of formula (I)+MAA, compound of formula (I)+MAMA, compound of formula (I)+MCPA, compound of formula (I)+MCPA-thioethyl, compound of formula (I)+MCPB, compound of formula (I)+mecoprop, compound of formula (I)+mecoprop-P, compound of formula (I)+mefenacet, compound of formula (I)+mefluidide, compound of formula (I)+mesosulfuron, compound of formula (I)+mesosulfuron-methyl, compound of formula (I)+mesotrione, compound of formula (I)+metam, compound of formula (I)+metamifop, compound of formula (I)+metamitron, compound of formula (I)+metazachlor, compound of formula (I) and metazosulfuron, compound of formula (I)+methabenzthiazuron, formula (I)+methazole, a compound of formula (I) and methiozolin, compound of formula (I)+methylarsonic acid, compound of formula (I)+methyldymron, compound of formula (I)+methyl isothiocyanate, compound of formula (I)+metobenzuron, formula (I)+metobromuron, compound of formula (I)+metolachlor, compound of formula (I)+S-metolachlor, compound of formula (I)+metosulam, compound of formula (I)+metoxuron, compound of formula (I)+metribuzin, compound of formula (I)+metsulfuron, compound of formula (I)+metsulfuron-methyl, compound of formula (I)+MK-616, compound of formula (I)+molinate, compound of formula (I)+monolinuron, a compound of formula (I) and monosulfuron, a compound of formula (I) and monosulfuron-ester compound of formula (I)+MSMA, compound of formula (I)+naproanilide, compound of formula (I)+napropamide, compound of formula (I)+naptalam, formula (I)+NDA-402989, compound of formula (I)+neburon, compound of formula (I)+nicosulfuron, formula (I)+nipyraclofen, formula (I)+n-methyl glyphosate, compound of formula (I)+nonanoic acid, compound of formula (I)+norflurazon, compound of formula (I)+oleic acid (fatty acids), compound of formula (I)+orbencarb, compound of formula (I)+orthosulfamuron, compound of formula (I)+oryzalin, compound of formula (I)+oxadiargyl, compound of formula (I)+oxadiazon, compound of formula (I)+oxasulfuron, compound of formula (I)+oxaziclomefone, compound of formula (I)+oxyfluorfen, compound of formula (I)+paraquat, compound of formula (I)+paraquat dichloride, compound of formula (I)+pebulate, compound of formula (I)+pendimethalin, compound of formula (I)+penoxsulam, compound of formula (I)+pentachlorophenol, compound of formula (I)+pentanochlor, compound of formula (I)+pentoxazone, compound of formula (I)+pethoxamid, compound of formula (I)+petrolium oils, compound of formula (I)+phenmedipham, compound of formula (I)+phenmedipham-ethyl, compound of formula (I)+picloram, compound of formula (I)+picolinafen, compound of formula (I)+pinoxaden, compound of formula (I)+piperophos, compound of formula (I)+potassium arsenite, compound of formula (I)+potassium azide, compound of formula (I)+pretilachlor, compound of formula (I)+primisulfuron, compound of formula (I)+primisulfuron-methyl, compound of formula (I)+prodiamine, compound of formula (I)+profluazol, compound of formula (I)+profoxydim, formula (I)+prohexadione-calcium, compound of formula (I)+prometon, compound of formula (I)+prometryn, compound of formula (I)+propachlor, compound of formula (I)+propanil, compound of formula (I)+propaquizafop, compound of formula (I)+propazine, compound of formula (I)+propham, compound of formula (I)+propisochlor, compound of formula (I)+propoxycarbazone, compound of formula (I)+propoxycarbazone-sodium, compound of formula (I)+propyzamide, compound of formula (I)+prosulfocarb, compound of formula (I)+prosulfuron, compound of formula (I)+pyraclonil, compound of formula (I)+pyraflufen, compound of formula (I)+pyraflufen-ethyl, formula (I)+pyrasulfotole, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyributicarb, compound of formula (I)+pyridafol, compound of formula (I)+pyridate, compound of formula (I)+pyriftalid, compound of formula (I)+pyriminobac, compound of formula (I)+pyriminobac-methyl, compound of formula (I)+pyrimisulfan, compound of formula (I)+pyrithiobac, compound of formula (I)+pyrithiobac-sodium, formula (I)+pyroxasulfone, formula (I)+pyroxulam, compound of formula (I)+quinclorac, compound of formula (I)+quinmerac, compound of formula (I)+quinoclamine, compound of formula (I)+quizalofop, compound of formula (I)+quizalofop-P, compound of formula (I)+quizalofop-ethyl, compound of formula (I)+quizalofop-P-ethyl, compound of formula (I)+rimsulfuron, compound of formula (I)+saflufenacil, compound of formula (I)+sethoxydim, compound of formula (I)+siduron, compound of formula (I)+simazine, compound of formula (I)+simetryn, compound of formula (I)+SMA, compound of formula (I)+sodium arsenite, compound of formula (I)+sodium azide, compound of formula (I)+sodium chlorate, compound of formula (I)+sulcotrione, compound of formula (I)+sulfentrazone, compound of formula (I)+sulfometuron, compound of formula (I)+sulfometuron-methyl, compound of formula (I)+sulfosate, compound of formula (I)+sulfosulfuron, compound of formula (I)+sulfuric acid, compound of formula (I)+tar oils, compound of formula (I)+2,3,6-TBA, compound of formula (I)+TCA, compound of formula (I)+TCA-sodium, formula (I)+tebutam, compound of formula (I)+tebuthiuron, formula (I)+tefuryltrione, compound of formula 1+tembotrione, compound of formula (I)+tepraloxydim, compound of formula (I)+terbacil, compound of formula (I)+terbumeton, compound of formula (I)+terbuthylazine, compound of formula (I)+terbutryn, compound of formula (I)+thenylchlor, compound of formula (I)+thiazafluron, compound of formula (I)+thiazopyr, compound of formula (I)+thifensulfuron, compound of formula (I)+thiencarbazone, compound of formula (I)+thifensulfuron-methyl, compound of formula (I)+thiobencarb, compound of formula (I)+tiocarbazil, compound of formula (I)+topramezone, compound of formula (I)+tralkoxydim, a compound of formula (I) and triafamone compound of formula (I)+tri-allate, compound of formula (I)+triasulfuron, compound of formula (I)+triaziflam, compound of formula (I)+tribenuron, compound of formula (I)+tribenuron-methyl, compound of formula (I)+tricamba, compound of formula (I)+triclopyr, compound of formula (I)+trietazine, compound of formula (I)+trifloxysulfuron, compound of formula (I)+trifloxysulfuron-sodium, compound of formula (I)+trifluralin, compound of formula (I)+triflusulfuron, compound of formula (I)+triflusulfuron-methyl, compound of formula (I)+trifop, compound of formula (I)+trifop-methyl, compound of formula (I)+trihydroxytriazine, compound of formula (I)+trinexapac-ethyl, compound of formula (I)+tritosulfuron, compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula (I)+2-[[8-chloro-3,4-dihydro-4-(4-methoxyphenyl)-3-oxo-2-quinoxalinyl]carbonyl-1,3-cyclohexanedione and the compound of formula (I)+VX-573.

In particular, the following mixtures are important:

mixtures of a compound of formula (I) with an acetanilide (e.g. compound of formula (I)+acetochlor, compound of formula (I)+dimethenamid, compound of formula (I)+metolachlor, compound of formula (I)+S-metolachlor, or compound of formula (I)+pretilachlor) or with other inhibitors of very long chain fatty acid esterases (VLCFAE) (e.g. compound of formula (I)+pyroxasulfone).

mixtures of a compound of formula (I) with an HPPD inhibitor (e.g. compound of formula (I)+isoxaflutole, compound of formula (I)+mesotrione, compound of formula (I)+pyrasulfotole, compound of formula (I)+sulcotrione, compound of formula (I)+tembotrione, compound of formula (I)+topramezone, compound of formula (I)+bicyclopyrone;

mixtures of a compound of formula (I) with a triazine (e.g. compound of formula (I)+atrazine, or compound of formula (I)+terbuthylazine);

mixtures of a compound of formula (I) with glyphosate;

mixtures of a compound of formula (I) with glufosinate-ammonium;

mixtures of a compound of formula (I) with a PPO inhibitor (e.g. compound of formula (I)+acifluorfen-sodium, compound of formula (I)+butafenacil, compound of formula (I)+carfentrazone-ethyl, compound of formula (I)+cinidon-ethyl, compound of formula (I)+flumioxazin, compound of formula (I)+fomesafen, compound of formula (I)+lactofen, or compound of formula (I)+SYN 523 ([3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Whilst two-way mixtures of a compound of formula (I) and another herbicide are explicitly disclosed above, the skilled man will appreciate that the invention extends to three-way, and further multiple combinations comprising the above two-way mixtures. In particular, the invention extends to:

mixtures of a compound of formula (I) with a triazine and an HPPD inhibitor (e.g. compound of formula (I)+triazine+isoxaflutole, compound of formula (I)+triazine+mesotrione, compound of formula (I)+triazine+pyrasulfotole, compound of formula (I)+triazine+sulcotrione, compound of formula (I)+triazine+tembotrione, compound of formula (I)+triazine+topramezone, compound of formula (I)+triazine+bicyclopyrone;

mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+bicyclopyrone;

mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+bicyclopyrone;

mixtures of a compound of formula (I) with a VLCFAE inhibitor and an HPPD inhibitor (e.g. compound of formula (I)+S-metolachlor+isoxaflutole, compound of formula (I)+S-metolachlor+mesotrione, compound of formula (I)+S-metolachlor+pyrasulfotole, compound of formula (I)+S-metolachlor+sulcotrione, compound of formula (I)+S-metolachlor+tembotrione, compound of formula (I)+S-metolachlor+topramezone, compound of formula (I)+S-metolachlor+bicyclopyrone, compound of formula (I)+acetochlor+isoxaflutole, compound of formula (I)+acetochlor+mesotrione, compound of formula (I)+acetochlor+pyrasulfotole, compound of formula (I)+acetochlor+sulcotrione, compound of formula (I)+acetochlor+tembotrione, compound of formula (I)+acetochlor+topramezone, compound of formula (I)+acetochlor+bicyclopyrone, compound of formula (I)+pyroxasulfone+isoxaflutole, compound of formula (I)+pyroxasulfone+mesotrione, compound of formula (I)+pyroxasulfone+pyrasulfotole, compound of formula (I)+pyroxasulfone+sulcotrione, compound of formula (I)+pyroxasulfone+tembotrione, compound of formula (I)+pyroxasulfone+topramezone, compound of formula (I)+pyroxasulfone+bicyclopyrone, compound of formula (I)+S-metolachlor+mesotrione+bicyclopyrone.

Mixtures of a compound of formula (I) with glyphosate and a VLCFAE inhibitor (e.g. compound of formula (I)+ glyphosate+S-metolachlor, compound of formula (I)+glyphosate+acetochlor, compound of formula (I)+glyphosate+pyroxasulfone).

Particularly preferred are mixtures of the compound of formula (I) with mesotrione, bicyclopyrone, isoxaflutole, tembotrione, topramezone, sulcotrione, pyrasulfotole, metolachlor, S-metolachlor, acetochlor, pyroxasulfone, P-dimethenamid, dimethenamid, flufenacet, pethoxamid, atrazine, terbuthylazine, bromoxynil, metribuzin, amicarbazone, bentazone, ametryn, hexazinone, diuron, tebuthiuron, glyphosate, paraquat, diquat, glufosinate, acifluorfen-sodium, butafenacil, carfentrazone-ethyl, cinidon-ethyl, flumioxazin, fomesafen, lactofen, [3-[2-chloro-4-fluoro-5-(1-methyl-6-trifluoromethyl-2,4-dioxo-1,2,3,4-tetrahydropyrimid in-3-yl)phenoxy]-2-pyridyloxy]acetic acid ethyl ester.

The mixing partners of the compound of formula (I) may also be in the form of esters or salts, as mentioned e.g. in The Pesticide Manual, 14th Edition (BCPC), 2006. The reference to acifluorfen-sodium also applies to acifluorfen, the reference to dimethenamid also applies to dimethenamid-P, the reference to glufosinate-ammonium also applies to glufosinate, the reference to bensulfuron-methyl also applies to bensulfuron, the reference to cloransulam-methyl also applies to cloransulam, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further active ingredients, in particular with one or more further herbicides, can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. Where a compound of formula (I) is combined with a safener, the following combinations of the compound of formula (I) and the safener are particularly preferred. Compound of formula (I)+AD 67 (MON 4660), compound of formula (I)+benoxacor, compound of formula (I)+cloquintocet-mexyl, compound of formula (I)+cyometrinil and a compound of formula (I)+the corresponding (Z) isomer of cyometrinil, compound of formula (I)+cyprosulfamide (CAS RN 221667-31-8), compound of formula (I)+dichlormid, compound of formula (I) and dicyclonon, compound of formula (I) and dietholate, compound of formula (I)+fenchlorazole-ethyl, compound of formula (I)+fenclorim, compound of formula (I)+flurazole, compound of formula (I)+fluxofenim, compound of formula (I)+furilazole and a compound of formula (I)+the corresponding R isomer or furilazome, compound of formula (I)+isoxadifen-ethyl, compound of formula (I)+mefenpyr-diethyl, compound of formula (I) and mephenate, compound of formula (I)+oxabetrinil, compound of formula (I)+naphthalic anhydride (CAS RN 81-84-5), compound of formula (1) and TI-35, compound of formula (I)+N-isopropyl-4-(2-methoxy-benzoylsulfamoyl)-benzamide (CAS RN 221668-34-4) and a compound of formula (I)+N-(2-methoxybenzoyl)-4-[(methylaminocarbonyl)amino]benzenesulfonamide. Particularly preferred are mixtures of a compound of formula (I) with benoxacor, a compound of formula (I) with cloquintocet-mexyl, a compound of formula (I)+cyprosulfamide and a compound of formula (I) with N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14th Edition (BCPC), 2006. The reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

Preferably the mixing ratio of compound of formula (1) to safener is from 100:1 to 1:10, especially from 20:1 to 1:1.

The mixtures can advantageously be used in the above-mentioned formulations (in which case "active ingredient" relates to the respective mixture of compound of formula (I) and any further active ingredient, in particular a further herbicide, with the safener).

It is possible that the safener and a compound of formula (I) and one or more additional herbicide(s), if any, are applied simultaneously. For example, the safener, a compound of formula (1) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with tembotrione and a safener.

Mixtures of a compound of formula (I) with topramezone and a safener.

Mixtures of a compound of formula (I) with bicyclopyrone and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with a triazine and tembotrione and a safener.

Mixtures of a compound of formula (I) with a triazine and topramezone and a safener.

Mixtures of a compound of formula (I) with a triazine and bicyclopyrone and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glyphosate and tembotrione and a safener.

Mixtures of a compound of formula (I) with glyphosate and topramezone and a safener.

Mixtures of a compound of formula (I) with glyphosate and bicyclopyrone and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with glufosinate-ammonium and tembotrione and a safener.

Mixtures of a compound of formula (I) with glufosinate-ammonium and topramezone and a safener.

Mixtures of a compound of formula (I) with glufosinate-ammonium and bicyclopyrone and a safener.

Mixtures of a compound of formula (I) with S-metolachlor and a safener.

Mixtures of a compound of formula (I) with S-metolachlor and isoxaflutole and a safener.

Mixtures of a compound of formula (I) with S-metolachlor and mesotrione and a safener.

Mixtures of a compound of formula (I) with S-metolachlor and sulcotrione and a safener.

Mixtures of a compound of formula (I) with S-metolachlor and tembotrione and a safener.

Mixtures of a compound of formula (I) with S-metolachlor and topramezone and a safener.

Mixtures of a compound of formula (I) with S-metolachlor and bicyclopyrone and a safener Mixtures of a compound of formula (I) with pyroxasulfone and a safener.

Mixtures of a compound of formula (I) with pyroxasulfone and isoxaflutole and a safener.

Mixtures of a compound of formula (I) with pyroxasulfone and mesotrione and a safener.

Mixtures of a compound of formula (I) with pyroxasulfone and sulcotrione and a safener.

Mixtures of a compound of formula (I) with pyroxasulfone and tembotrione and a safener.

Mixtures of a compound of formula (I) with pyroxasulfone and topramezone and a safener.

Mixtures of a compound of formula (I) with pyroxasulfone and bicyclopyrone and a safener.

Mixtures of a compound of formula (I) with acetochlor and a safener.

Mixtures of a compound of formula (I) with acetochlor and isoxaflutole and a safener.

Mixtures of a compound of formula (I) with acetochlor and mesotrione and a safener.

Mixtures of a compound of formula (I) with acetochlor and sulcotrione and a safener.

Mixtures of a compound of formula (I) with acetochlor and tembotrione and a safener.

Mixtures of a compound of formula (I) with acetochlor and topramezone and a safener.

Mixtures of a compound of formula (I) with acetochlor and bicyclopyrone and a safener.

Mixtures of a compound of formula (I) with S-metolachlor and mesotrione and bicyclopyrone and a safener.

Mixtures of a compound of formula (I) with S-metolachlor and a triazine and mesotrione and bicyclopyrone and a safener.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Preparation Examples

The following abbreviations were used in this section: s=singlet; bs=broad singlet; d=doublet; dd=double doublet; dt=double triplet; t=triplet, tt=triple triplet, q=quartet, sept=septet; m=multiplet; RT=retention time, MH$^+$=molecular mass of the molecular cation.

1H NMR spectra were recorded at 400 MHz either on a Varian Unity Inova instrument 400 MHz or on a Bruker AVANCE-II instrument.

Where $R_2$ is not H, the compounds may exist in a mixture of diastereoisomers, which may be observed by LC-MS and NMR. The stereochemistry of the chiral centre at the carbon containing the $R_3$ group was generally found to interconvert at room temperature. Depending on the nature of $R_2$ substitution and the conditions for product synthesis, purification and analysis the ratio of diastereomers may change.

Example 1

Preparation of 1-[6-chloro-5-(1-fluoro-1-methylethyl)pyridazin-3-yl]-5-hydroxy-3,4-dimethyl-imidazolidin-2-one (A2)

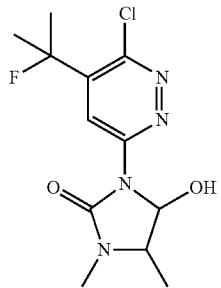 [SMILES: CC1C(O)N(c2cc(C(C)(C)F)c(Cl)nn2)C(=O)N1C]

Procedure for Synthesis of 1,1-dimethoxy-N-methyl-propan-2-amine (Step 1)

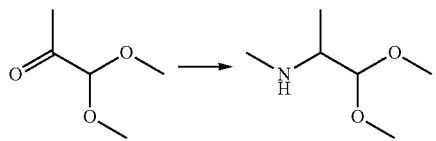

Ti(O-iPr)$_4$ (34.3 g, 2 equiv.) was cooled to 10° C. under a nitrogen atmosphere then ethanol (89 mL) was added followed by 1,1-dimethoxypropan-2-one (7.14 g, 1 equiv), methylamine hydrochloride (8.16 g, 2 equiv.) and triethylamine (16.8 mL, 2 equiv.). The reaction was stirred at room temperature for 15 h. The reaction was cooled to 10° C. and then NaBH$_4$ (3.43 g, 1.5 equiv.) was added and the reaction was stirred at room temperature for 6 h. The reaction was cooled to 10° C., then carefully over 10 minutes poured into ice cold aqueous ammonia (180 mL, 2M). The mixture was filtered, washing through with DCM (300 mL). The layers were separated and then the aqueous layer was extracted with further DCM (3×100 mL). The combined DCM layers were dried (Na$_2$SO$_4$), filtered and evaporated with care as to not lose any of the volatile product. This crude material was distilled on a Kugelrohr (70 to 110° C. 14 mBar) to give product (4.41 g) as a colourless oil, which was used without further purification.

$^1$H NMR (CDCl$_3$): 4.11 (d, 1H), 3.41 (s, 6H), 2.69 (pentet, 1H), 2.43 (s, 3H), 1.06 (d, 3H).

Procedure for Synthesis of 1-(2,2-dimethoxy-1-methyl-ethyl)-1-methyl-urea (Step 2)

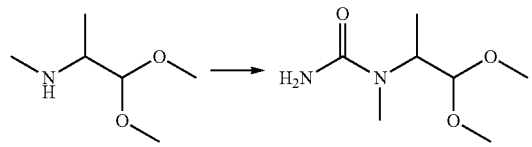

1,1-dimethoxy-N-methyl-propan-2-amine (1.0 g, 7.50 mmol) was dissolved in CDCl$_3$ (1.5 mL). Trimethylsilyl isocyanate (commercially available) (2 equiv.) was added and the reaction was stirred at room temp for 4 days. The reaction mixture heated to reflux for 160 minutes while incrementally adding a further trimethylsilyl isocyanate (1.5 equiv.) The reaction was evaporated and treated with water (10 mL), stirred for 90 minutes, then evaporated to give crude product (1.08 g) which was used without further purification.

$^1$H NMR: 4.60 (br s, 2H), 4.30 (br s, 1H), 4.24 (d, 1H), 3.41 (s, 6H), 2.71 (s, 3H), 1.18 (d, 3H).

Procedure for Synthesis of 3,6-dichloro-4-(1-fluoro-1-methyl-ethyl)pyridazine (Step-3)

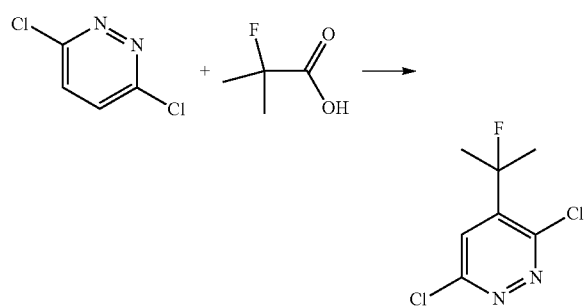

3,6-dichloropyridazine (commercially available) (16.0 g, 107 mmol) was slurried with 2-fluoro-2-methyl-propanoic acid (22.8 g, 215 mmol) in conc. sulfuric acid (15.8 g, 161 mmol) in water (100 mL) and the mixture was warmed to 40° C. Silver nitrate (1.82 g, 10.7 mmol) was added and the mixture heated to 62° C. Then ammonium persulphate (42.1 g, 183 mmol) in water (200 mL) was added dropwise over 60 mins. The reaction mixture was heated to 80° C. for a further 60 mins before cooling to approximately 15° C. with an ice bath. Ice was added to the reaction and pH was adjusted the 9 with ammonium hydroxide (~100 mL). The mixture was stirred for ~15 mins then extracted with diethyl ether (3×250 mL). The combined organics were dried and evaporated to give an orange oil which solidified on standing. This crude material was chromatographed on silica eluting with 0-25% EtOAc in isohexane. Fractions containing product were evaporated to give desired product as a colourless oil which solidified on standing (12.6 g, 56%).

LC-MS: (positive ES MH+209/211).

Procedure for Synthesis of 3-[6-chloro-5-(1-fluoro-1-methyl-ethyl)pyridazin-3-yl]-1-(2,2-dimethoxy-1-methyl-ethyl)-1-methyl-urea (Step 4)

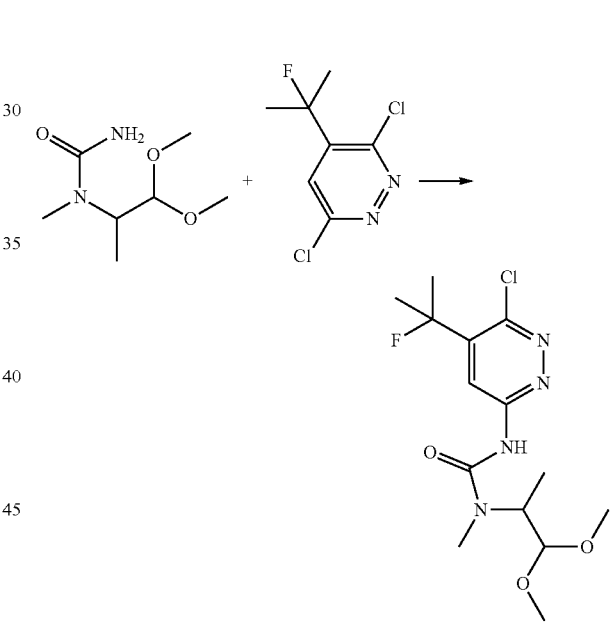

1-(2,2-dimethoxy-1-methyl-ethyl)-1-methyl-urea (200 mg, 1.249 mmol), 3,6-dichloro-4-(1-fluoro-1-methyl-ethyl)pyridazine (285 mg, 1.2 equiv.), potassium carbonate (235 mg, 1.5 equiv.), tris(dibenzylideneacetone)dipalladium(0) (43 mg), 4,5-bis(diphenylphosphino)-9,9-dimethylxanthene (101 mg) were suspended in 1-4-dioxane (6 mL) and the mixture was then heated at 105° C. in a sealed vial for 1 h. The mixture was allowed to cool to room temperature, diluted with EtOAc, filtered then chromatographed on silica eluting with 10-35% EtOAc in isohexane. Fractions containing product were evaporated to give the desired product as a colourless gum (190 mg, 48%).

LC-MS: (positive ES MH+349/351).

Procedure for Synthesis of 1-[6-chloro-5-(1-fluoro-1-methyl-ethyl)pyridazin-3-yl]-5-hydroxy-3,4-dimethyl-imidazolidin-2-one (Step-5)

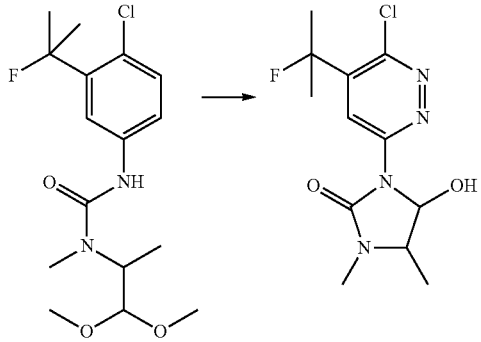 [SMILES: COC(OC)C(C)N(C)C(=O)Nc1ccc(Cl)c(C(C)(C)F)c1 ; CC1C(O)N(c2cc(C(C)(C)F)c(Cl)nn2)C(=O)N1C]

3-[6-chloro-5-(1-fluoro-1-methyl-ethyl)pyridazin-3-yl]-1-(2,2-dimethoxy-1-methyl-ethyl)-1-methyl-urea (190 mg, 0.545 mmol) was dissolved in acetic acid (6 mL), then water (3 mL) was added to give a homogeneous solution. This was stirred at room temperature for 2 days and then at 60° C. for 25 mins. The reaction was evaporated (100 to 1 mBar at 20-35° C. for 2 h) and azeotroped with toluene to remove traces of HOAc to give product (139 mg, 84%).

LC-MS: (positive ES MH+303/305).
$^1$H NMR (CDCl$_3$): Major diastereomer: 8.80 (s, 1H), 5.71 (m, 1H), 4.85 (br s, 1H), 3.57 (m, 1H), 2.95 (s, 3H), 1.88 (d, 3H), 1.82 (d, 3H), 1.36 (d, 3H).

Minor diastereomer: 8.80 (s, 1H), 6.09 (d, 1H), 4.70 (br s, 1H), 3.82 (pentet, 1H), 2.90 (s, 3H), 1.89 (d, 3H), 1.82 (d, 3H), 1.41 (d, 3H).

Example 2

Preparation of 1-[6-chloro-5-(1-fluoro-1-methyl-ethyl)pyridazin-3-yl]-5-hydroxy-3,4-dimethyl-imidazolidin-2-one (A3)

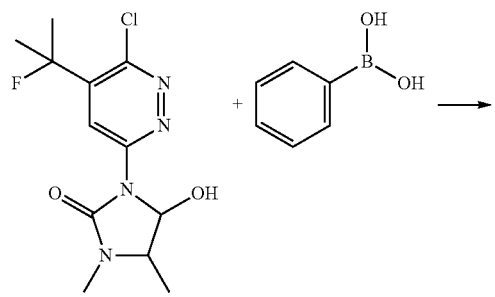

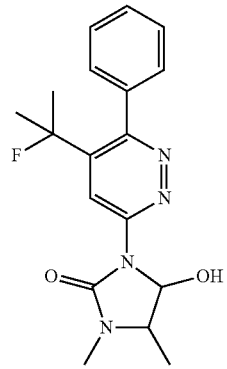

1-[6-chloro-5-(1-fluoro-1-methyl-ethyl)pyridazin-3-yl]-5-hydroxy-3,4-dimethyl-imidazolid in-2-one (75 mg, 1 equiv. 0.248 mmol), phenylboronic acid (39 mg, 1.3 equiv.), 2-Dicyclohexylphosphino-2',6'-dimethoxybiphenyl (S-Phos) (15 mg, 0.15 equiv.) Pd$_2$(OAc)$_2$ (5 mg, 0.1 equiv.), in 1,4-dioxane (1.3 mL) was treated with K$_3$PO$_4$ (79 mg). The reaction was heated for 25 mins at 70° C., and then 25 mins at 90° C. The reaction mixture was diluted with EtOAc (5 mL) then filtered through celite, evaporated, then chromatographed on silica eluting with 20-100% EtOAc in isohexane. Fractions containing product were evaporated to give desired product as a beige solid (55 mg, 60%).

LC-MS: (positive ES MH+345).
$^1$H NMR (CDCl$_3$): Major diastereomer: 8.71 (s, 1H), 7.45 (m, 3H), 7.39 (m, 2H), 5.80 (s, 1H), 5.18 (br s, 1H), 3.59 (m, 1H), 2.96 (s, 3H), 1.57 (d, 3H), 1.52 (d, 3H), 1.36 (d, 3H).

Minor diastereomer: 8.71 (s, 1H), 7.45 (m, 3H), 7.39 (m, 2H), 6.15 (d, 1H), 5.05 (br s, 1H), 3.82 (pentet, 1H), 2.92 (s, 3H), 1.57 (d, 3H), 1.52 (d, 3H), 1.41 (d, 3H).

Example 3

Preparation of 3-[6-chloro-5-(trifluoromethyl)pyridazin-3-yl]-4-hydroxy-1-methyl-imidazolidin-2-one (A5)

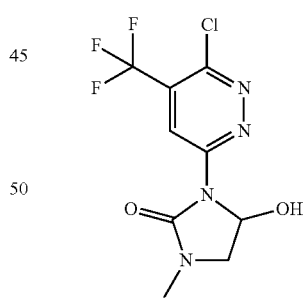

Procedure for Synthesis of 1-(2,2-dimethoxyethyl)-1-methyl-urea (Step-1)

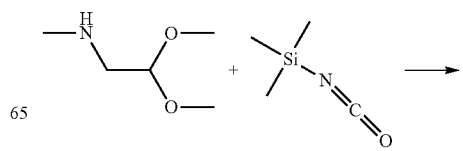

-continued

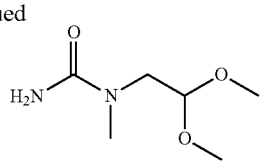

A solution of (methylamino)acetaldehyde dimethyl acetal ((commercially available) (20 g, 0.167 mol) in DCM (46 mL) was treated with trimethylsilyl isocyanate (commercially available) (46 mL, 335 mmol) over 15 mins, keeping internal temperature below 25° C. The reaction was then left to stir at room temperature for 8 days. Reaction was evaporated at reduced pressure (100 to 1 mBar with liquid $N_2$ trap at 20 to 40° C.) to give a white solid/gum mix, which was dissolved in 100 ml water. After 22 h, was evaporated at reduced pressure (1 mbar at 30-40° C.) and left dry for 8 h under these conditions to give product as a tacky white solid mass (26.0 g, 95% yield).

$^1$H NMR (CDCl$_3$): 4.80 (br s, 2H), 4.45 (t, 1H), 3.44 (s, 6H), 3.36 (d, 2H), 2.96 (s, 3H).

Procedure for Synthesis of 3-[6-chloro-5-(trifluoromethyl)pyridazin-3-yl]-1-(2,2-dimethoxyethyl)-1-methyl-urea (Step-2)

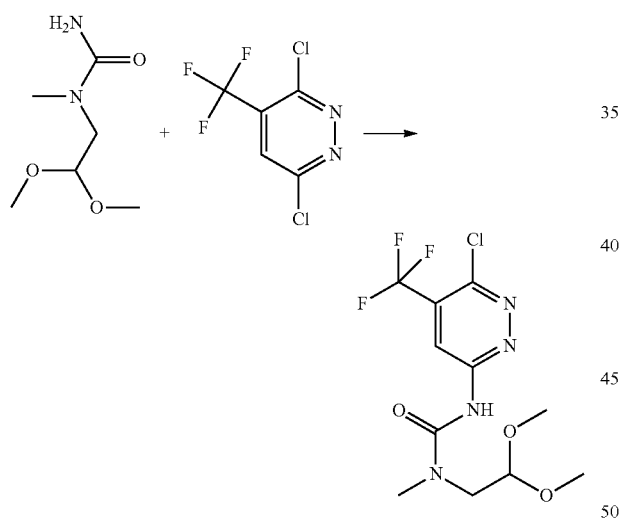

A mixture of 1-(2,2-dimethoxyethyl)-1-methyl-urea ((262 mg, 1.613 mmol), 3,6-dichloro-4-(trifluoromethyl) pyridazine (commercially available) (250 mg, 1.152 mmol), tris(dibenzylideneacetone)dipalladium(0) (33.8 mg, 0.0375 mmol), 4,5-bis(diphenylphosphino)-9,9-dimethylxanthene (69.5 mg, 0.115 mmol), and K$_2$CO$_3$ (318 mg, 2.304 mmol) in 1,4-dioxane (2.5 mL) under a Nitrogen atmosphere was heated at 75° C. for 1 h. The mixture was allowed to cool to room temperature, filtered then chromatographed on silica eluting with 0-100% EtOAc in isohexane. Fractions containing product were evaporated to give desired product a colourless oil (40 mg, 10%), which was without further purification in the next reaction.

$^1$HNMR (CDCl$_3$): 8.59 (br s, 1H), 4.52 (t, 1H), 3.45-3.58 (m, 8H), 3.11 (s, 3H).

Procedure for Synthesis of 3-[6-chloro-5-(trifluoromethyl)pyridazin-3-yl]-4-hydroxy-1-methyl-imidazolidin-2-one (Step-3)

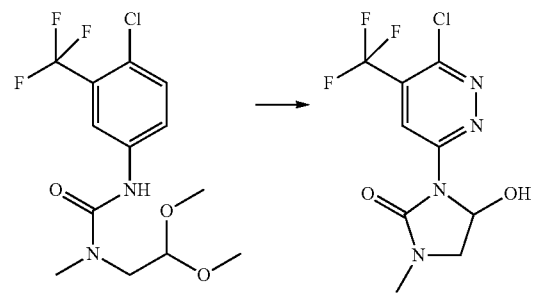 [SMILES: COC(CN(C)C(=O)Nc1ccc(Cl)c(C(F)(F)F)c1)OC ; CN1CC(O)N(c2cc(C(F)(F)F)c(Cl)nn2)C1=O]

A solution of 3-[6-chloro-5-(trifluoromethyl)pyridazin-3-yl]-1-(2,2-dimethoxyethyl)-1-methyl-urea (40 mg, 0.117 mmol) in acetic acid (1 mL) was treated with water (0.5 mL) and then heated to 80° C. for 30 mins and then to 95° C. for 2 h. The reaction mixture was evaporated and azeotroped with toluene. The crude product was chromatographed on silica (eluting with with 0-100% EtOAc in isohexane. Fractions containing product were evaporated to give the desired product (34 mg, 98%).

LC-MS: (positive ES MH+297/299).

$^1$H NMR (CDCl$_3$): 8.98 (1H, s), 6.23 (1H, dd), 4.76 (1H, br. s.), 3.80 (1H, dd), 3.47 (1H, dd), 2.99 (3H, s).

Example 4

4-hydroxy-1-methyl-3-[5-(trifluoromethyl)pyridazin-3-yl]imidazolidin-2-one (A7)

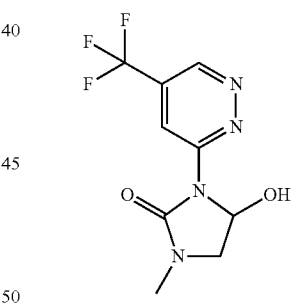

3-[6-chloro-5-(trifluoromethyl)pyridazin-3-yl]-4-hydroxy-1-methyl-imidazolidin-2-one (0.0500 g, 0.169 mmol), sodium formate (0.0233 g, 0.337 mmol), Pd(OAc)$_2$ (0.000378 g, 0.00168 mmol) in acetonitrile (3 mL) and water (0.5 mL) were mixed in a microwave vial and heated at 150° C. for 20 mins. Further Pd(OAc)$_2$ (3 mg) was added and the mixture heated in the microwave at 150° C. for a further 60 mins. The reaction mixture was concentrated in vacuo to remove most of the MeCN, then partitioned between DCM (15 mL) and brine (15 mL). The mixture was passed through a phase separation cartridge then the DCM layer was dry-loaded onto silica. The crude product was chromatographed on silica (eluting with with 0-100% EtOAc in isohexane. Fractions containing product were evaporated to give the desired product (31 mg, 71%).

LC-MS: (positive ES MH+263).

¹H NMR (CDCl₃): 9.06 (d, 1H), 8.84 (m, 1H), 6.26 (dt, 1H), 4.89 (d, 1H), 3.79 (m, 1H), 3.48 (dd, 1H), 2.99 (s, 3H).

Example 5

Preparation of 1-[6-chloro-5-(1-fluoro-1-methyl-ethyl)pyridazin-3-yl]-5-hydroxy-3-methoxy-4-methyl-imidazolidin-2-one (A6)

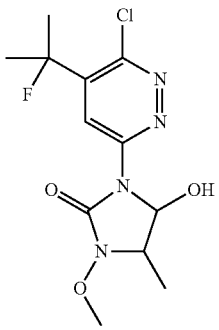 [SMILES: CON1C(=O)N(c2cc(C(C)(C)F)c(Cl)nn2)C(O)C1C]

Procedure for Synthesis of
N,1,1-trimethoxypropan-2-imine (Step-1)

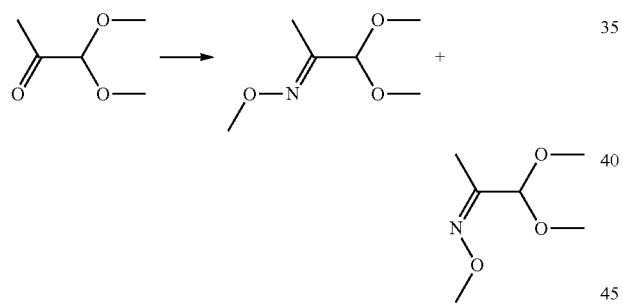

Methoxylamine hydrochloride (21.2 g) was suspended in methanol (65 mL) then potassium acetate (50.4 g, quickly ground in pestle and mortar to break up lumps) was added all at once and the thick white suspension resulting was stirred at room temp for 15 mins then cooled to 15° C. and then 1,1-dimethoxypropan-2-one (30 g) was added slowly over 25 mins. The reaction was stirred at room temperature for 50 mins and then diluted with 200 ml DCM, then 100 ml sat. NaHCO₃ (aq) was added cautiously over 15 mins. After effervescence subsided, the layers were separated, extracted with further DCM (2×80 mL), dried Na₂SO₄, filtered and concentrated at 220 mbar and 35° C. (care as desired product is volatile) to give 37 g amber liquid, which was used without further purification.

¹H NMR (CDCl₃) showed a 3:1 ratio of E:Z isomers

Procedure for Synthesis of
N,1,1-trimethoxypropan-2-amine (Step-2)

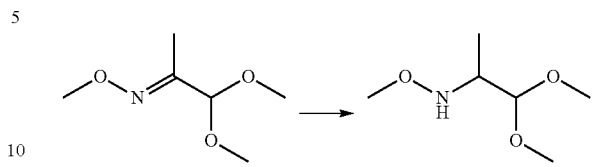

N,1,1-trimethoxypropan-2-imine (20 g) was dissolved in acetic acid (80 mL) then was cooled to 13° C. NaBH₃CN (9.82 g) was added portionwise over 10 mins. After 18 hrs at room temperature, the reaction was concentrated to remove bulk of HOAc then residue dissolved in DCM (300 mL) and satd. NaHCO₃ (aq) (300 mL) was added slowly with stirring. The mixture was stirred at rt for 90 mins, and then 40% NaOH(aq) was added until the solution reached pH 12. The layers were separated, extracted with further DCM (3×100 mL). The combined DCM layers were dried (Na₂SO₄), filtered and evaporated to give 16.4 g of crude product as a pale amber oil, which was further purified by Kugelrohr distillation (120° C. at 70 mBar) to give product (12.0 g, 59% yield) which was approximately 95% pure by NMR and used without further purification.

Procedure for Synthesis of 1-(2,2-dimethoxy-1-methyl-ethyl)-1-methoxy-urea (Step-3)

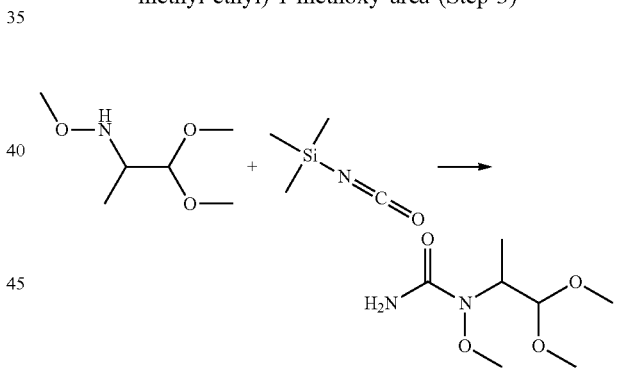

N,1,1-trimethoxypropan-2-amine (2.000 g, 13.41 mmol) was dissolved in IPA (5 mL) and the mixture was cooled to 0° C. under N₂, then trimethylsilyl isocyanate (commercially available) (4.83 mL, 33.51 mmol) was added and the reaction was allowed to warm to room temperature and was stirred at room temperature for 24 h. The reaction mixture was worked up by adding DCM (30 mL) and water (15 mL), extracting with further DCM (2×15 mL), dried (Na₂SO₄), filtered and evaporated then chromatographed on silica eluting with 50-100% EtOAc in isohexane. Fractions containing product were evaporated to give the desired product as a white solid (2.08 g, 81% yield).

1H NMR (CDCl₃): 5.36 (br s, 2H), 4.47 (d, 1H), 4.32 (pentet, 1H), 3.75 (s, 3H), 3.37 (d, 6H), 1.24 (d, 3H).

Procedure for Synthesis of 1-(2,2-dimethoxy-1-methyl-ethyl)-1-methoxy-3-[4-(trifluoromethyl)-2-pyridyl]urea (Step-4)

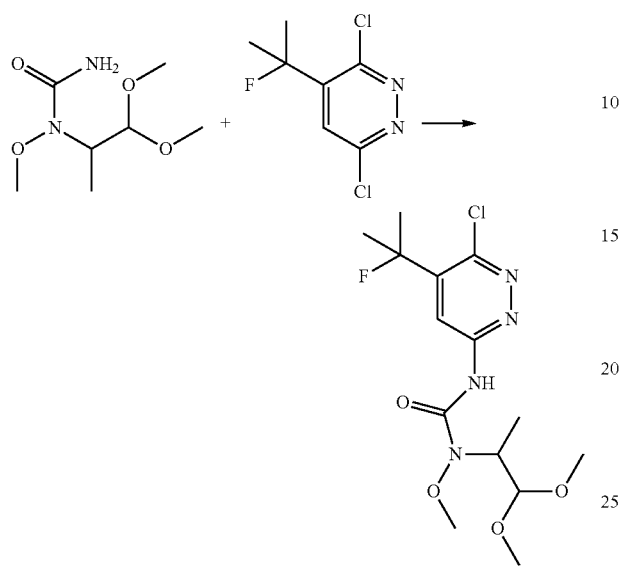

1-(2,2-dimethoxy-1-methyl-ethyl)-1-methoxy-urea (100 mg, 0.56 mmol), 3,6-dichloro-4-(1-fluoro-1-methyl-ethyl)pyridazine (109 mg, 1.1 equiv.), cesium carbonate (246 mg, 1.5 equiv.), [(4,5-bis(diphenylphosphino)-9,9-dimethylxanthene)-2-(2'-amino-1,1'-biphenyl)]palladium(II) methanesulfonate (10 mg) were suspended in 1-4-dioxane (1 mL) and the mixture was degassed (by bubbling $N_2$ through solution) and then heated at 80° C. in a sealed vial for 65 mins. The mixture was allowed to cool to room temperature, diluted with EtOAc, filtered, then chromatographed on silica eluting with 0-40% EtOAc in isohexane. Fractions containing product were evaporated to give the desired product as a yellow gum.

LC-MS: (positive ES MH+365/367).

Procedure for Synthesis of 1-[6-chloro-5-(1-fluoro-1-methyl-ethyl)pyridazin-3-yl]-5-hydroxy-3-methoxy-4-methyl-imidazolidin-2-one (Step-5)

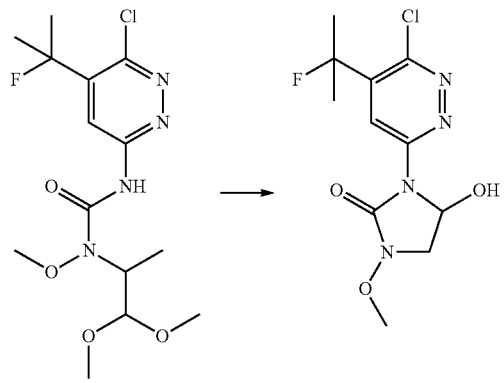 [SMILES: COC(OC)C(C)N(OC)C(=O)Nc1cc(C(C)(C)F)c(Cl)nn1 ; CON1CC(O)N(c2cc(C(C)(C)F)c(Cl)nn2)C1=O]

1-(2,2-dimethoxy-1-methyl-ethyl)-1-methoxy-3-[4-(trifluoromethyl)-2-pyridyl]urea (100 mg) was dissolved in 1,4-dioxane (1 mL) and 2N HCl (0.5 mL) was added and the reaction was stirred at 50° C. for 35 mins. Reaction mixture was treated with DCM (10 mL) and water (3 mL) and the aqueous was further extracted with DCM (2×4 mL). The combined DCM fractions were dried ($Na_2SO_4$), filtered, evaporated and then chromatographed on silica eluting with 0-20% EtOAc in isohexane. Fractions containing product were evaporated to give the desired product as a pale beige solid (76 mg, 76%).

LC-MS: (positive ES MH+319/321).

NMR indicated a ratio of diastereoisomers in approximately a 2:1 ratio.

$^1$H NMR (CDCl$_3$): Major diastereomer: 8.80 (s, 1H), 5.68 (m, 1H), 4.95 (br s, 1H), 3.88 (s, 3H), 3.58 (m, 1H), 1.88 (s, 3H), 1.82 (d, 3H), 1.48 (d, 3H).

Minor diastereomer: 8.80 (s, 1H), 6.01 (m, 1H), 4.65 (br s, 1H), 3.92 (s, 3H), 3.82 (m, 1H), 1.88 (s, 3H), 1.82 (d, 3H), 1.51 (d, 3H).

Example 6

Preparation of 1-[6-chloro-5-(1-fluoro-1-methyl-ethyl)pyridazin-3-yl]-4-ethoxy-5-hydroxy-3-methyl-imidazolidin-2-one (A9)

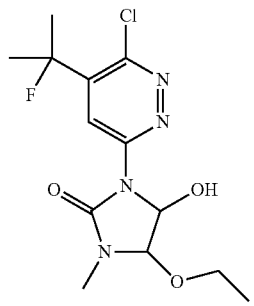 [SMILES: CCOC1C(O)N(c2cc(C(C)(C)F)c(Cl)nn2)C(=O)N1C]

Procedure for Synthesis of 1-[6-chloro-5-(1-fluoro-1-methyl-ethyl)pyridazin-3-yl]-3-methyl-urea (Step-1)

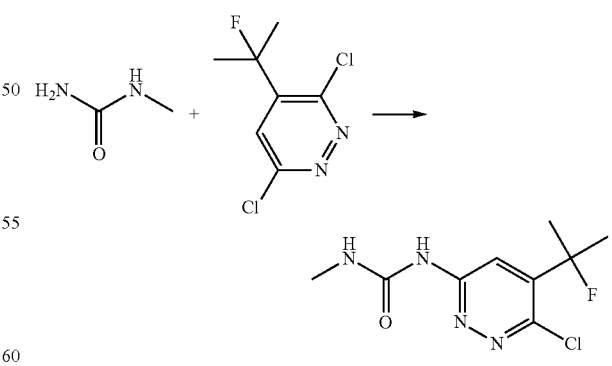

A mixture of tris(dibenzylideneacetone)dipalladium(0) (0.065 g, 0.78 mmol), 4,5-bis(diphenylphosphino)-9,9-dimethylxanthene (0.163 g, 0.273 mmol), potassium carbonate (2.01 g, 14.4 mmol) and methylurea (0.797 g, 10.8 mmol) in 1,4-dioxane (20 mL) was treated with 3,6-dichloro-4-(1-fluoro-1-methyl-ethyl)pyridazine (1.50 g, 7.18 mmol), The mixture was warmed to 85-90° C. with stirring under a Nitrogen atmosphere for 3.5 h. The reaction mixture was diluted with EtOAc (30 mL) and water (20 mL) and filtered through a pad of celite, rinsing through with further small portions of EtOAc and water. The organic extracts were combined, washed with brine (15 mL), dried over MgSO$_4$, filtered and the filtrate evaporated giving an orange liquid. This was chromatographed (eluting with an EtOAc/iso-hexane gradient) and fractions containing product were evaporated and triturated with iso-hexane to give the desired product as a light yellow-pink powder (0.67 g, 38%).

LC-MS: (positive ES MH+247/249).

Procedure for Synthesis of 1-[6-chloro-5-(1-fluoro-1-methyl-ethyl)pyridazin-3-yl]-4-ethoxy-5-hydroxy-3-methyl-imidazolidin-2-one (Step-2)

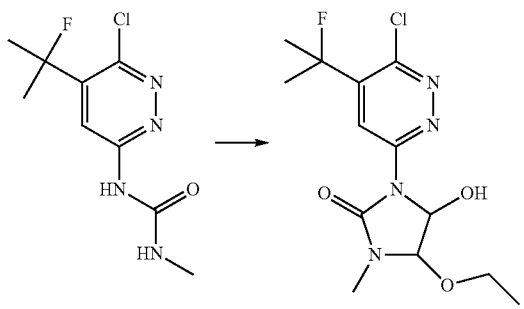 [SMILES: CNC(=O)Nc1cc(C(C)(C)F)c(Cl)nn1 ; CCOC1C(O)N(c2cc(C(C)(C)F)c(Cl)nn2)C(=O)N1C]

To 1-[6-chloro-5-(1-fluoro-1-methyl-ethyl)pyridazin-3-yl]-3-methyl-urea (0.325 g, 1.32 mmol) in ethanol (10 mL) was added glyoxal (40% aqueous solution) (1.15 g, 7.91 mmol, 0.907 mL) and 4-methylbenzenesulfonic acid (0.0113 g, 0.0659 mmol). The mixture was then warmed and heated at reflux for 5.5 hours and then allowed stand at room temperature overnight. The reaction mixture was concentrated to give a syrupy residue. This was dissolved in DCM (15 mL) and washed with brine (2×5 mL). The organic phase was dried (MgSO$_4$) filtered and the filtrate concentrated giving the crude product as a dark green gum (1.07 g). The crude product was dissolved in DCM (20 mL) then chromatographed on silica eluting with methanol in DCM. Fractions containing product were evaporated and triturated to give 1-[6-chloro-5-(1-fluoro-1-methyl-ethyl)pyridazin-3-yl]-4-ethoxy-5-hydroxy-3-methyl-imidazolidin-2-one as a white solid (0.160 g, 37%).

LC-MS: (positive ES MH+333/335).

$^1$H NMR (CDCl$_3$): 8.73 (s, 1H); 5.85 (d, 1H); 4.78 (d, 1H); 4.74 (s, 1H); 3.67 (ddq, 2H); 3.01 (s, 3H); 1.86 (d, 3H); 1.81 (d, 3H); 1.28 (t, 3H)

Example 7

Preparation of 3,6-dichloro-4-(1,1-difluoroethyl)pyridazine as used for synthesis of examples of the type A10, A11 and A12

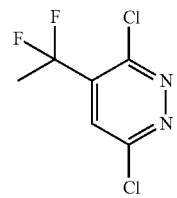

Procedure for Synthesis of 1-(3,6-dichloropyridazin-4-yl)ethanone (Step-1)

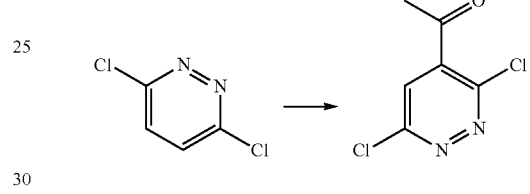

A mixture of 3,6-dichloropyridazine (30 g, 201.3693 mmol) and acetaldehyde (17.74 g, 2 equiv., 402.74 mmol) in acetic acid (300 mL) was cooled to −10° C., and treated with an ice cold mixture of conc sulfuric acid (60 mL) and water (300 mL). To this mixture was added dropwise a suspension of ferrous sulfate (61.18 g, 402.74 mmol) and ammonium persulphate (92.83 g. 402.74 mmol) in water (180 mL) maintaining a reaction temperature between −10° C. to 5° C. The reaction was stirred for two hrs at 0° C. The reaction was then extracted with ethyl acetate (3×150 mL). The combined organic fractions were washed with water (2×50 mL), dried (Na$_2$SO$_4$) and concentrated to give crude product (16 g) which was used without further purification.

LC-MS: (positive ES MH+191/193).

Procedure for Synthesis of 3,6-dichloro-4-(1,1-difluoroethyl)pyridazine (Step-2)

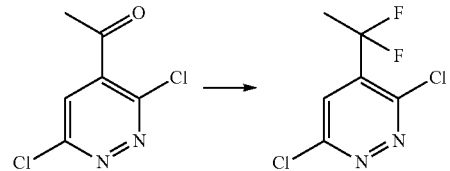

To a stirred solution of crude 1-(3,6-dichloropyridazin-4-yl)ethanone (16 g) in dry dichloromethane (320 mL) was added diethylaminosulfur trifluoride (25.58 g 150.77 mmol) at 0° C. and the reaction was then stirred at rt overnight. The reaction mixture was slowly added to cold saturated aqueous sodium bicarbonate solution. This was then extracted with dichloromethane (3×90 mL). The combined organic fractions were dried (Na$_2$SO$_4$) and evaporated. The crude product was dissolved in ethyl acetate then chromatographed on silica eluting with ethyl acetate in Hexane. Fractions containing product were evaporated to give 3,6-dichloro-4-(1,1-difluoroethyl)pyridazine as a white solid (4.8 g, 45%).

LC-MS: (positive ES MH+213/215).

Example 8

Preparation of 6-chloro-N-(1-cyano-1-methyl-ethyl)pyridazine-3-carboxamide as Used for Synthesis of Examples of the Type A13

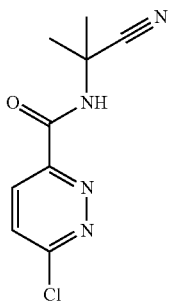

Procedure for Synthesis of 6-chloropyridazine-3-carboxylic acid (Step-1)

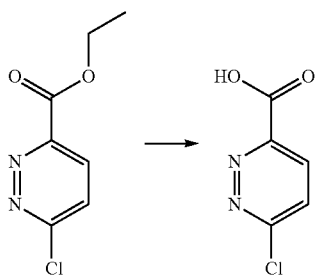

To a mixture of ethyl 6-chloropyridazine-3-carboxylate (commercially available) (1.00 g, 5.36 mmol) in THF (10 mL) was added LiOH (0.655 g, 26.8 mmol, 5 equiv.) in water (10 mL). The resulting reaction mixture was stirred at ambient temperature for 45 mins. The reaction mixture was poured into 2M hydrochloric acid and extracted with DCM. The organics were combined and evaporated to give product as a white solid (770 mg, 91%).

LC-MS: (positive ES MH+159/161).

Procedure for Synthesis of 6-chloro-N-(1-cyano-1-methyl-ethyl)pyridazine-3-carboxamide (Step-2)

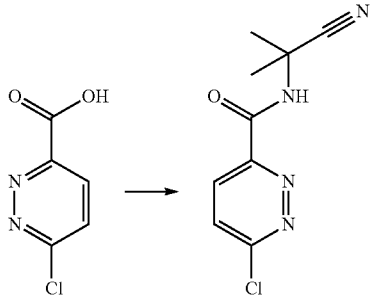

To a mixture of 6-chloropyridazine-3-carboxylic acid (0.770 g, 4.86 mmol) in DCM (10 mL) was added oxalyl chloride (0.629 g, 4.86 mmol) dropwise. DMF (0.050 mL) was added and the resulting reaction mixture was stirred at ambient temperature for 1 h. The reaction mixture was evaporated in vacuo to give the intermediate acid chloride (6-chloropyridazine-3-carbonyl chloride). To a mixture of 6-chloropyridazine-3-carbonyl chloride (0.835 g, 4.72 mmol) and N,N'-diisopropylethylamine (0.610 g, 4.72 mmol, 1 equiv.) in DCM (10 mL), was added 2-amino-2-methyl-propanenitrile (0.397 g, 4.72 mmol, 1 equiv.) dropwise. The resulting reaction mixture was stirred at ambient temperature for 18 h. The reaction mixture was then poured into water and extracted with DCM. The organics were combined and evaporated in vacuo and the crude product then chromatographed on silica eluting with 0-80% EtOAc in isohexane. Fractions containing product were evaporated to give the desired product as a white solid (606 mg, 75%). LC-MS: (positive ES MH+225/227).

Example 9

Preparation of N-tert-butyl-6-chloro-pyridazine-3-carboxamide as Used for Synthesis of Examples of the Type A14 and A15

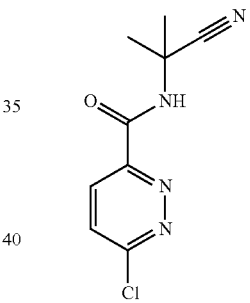

Procedure as for example 8, but using 2-methylpropan-2-amine instead of 2-amino-2-methyl-propanenitrile.

Tables 1 and 2 list examples of compounds of the general formula (I)

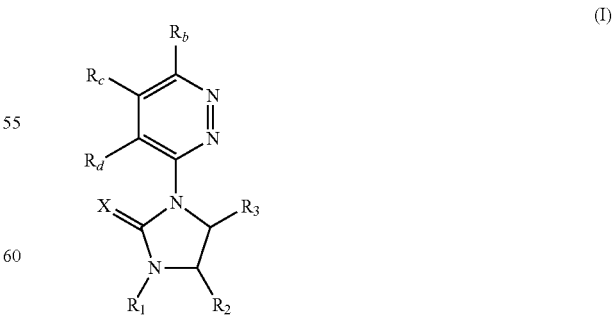

wherein $R^b$, $R^c$, $R^d$, $R^1$, $R^2$, $R^3$ and X are as defined above.

These compounds were made by the general methods described.

TABLE 1

| Example | STRUCTURE | 1H NMR (measured in CDCl₃ unless otherwise indicated) δ | LC-MS |
|---------|-----------|---------------------------------------------------------|-------|
| A1 | 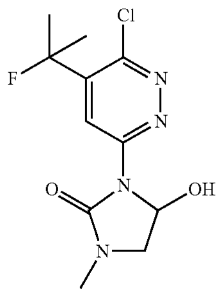 | 8.80 (s, 1H), 6.19 (m, 1H), 4.88 (m, 1H), 3.76 (dd, 1H), 3.43 (dd, 1H), 2.98 (s, 3H), 1.87 (d, 3H), 1.82 (d, 3H). | positive ES MH+ 289/291 |
| A2 | 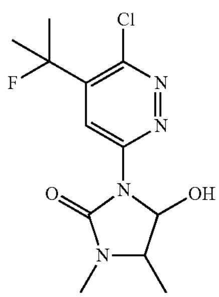 [SMILES: CC1C(O)N(c2cc(C(C)(C)F)c(Cl)nn2)C(=O)N1C] | Major diastereomer: 8.80 (s, 1H), 5.71 (m, 1H), 4.85 (br s, 1H), 3.57 (m, 1H), 2.95 (s, 3H), 1.88 (d, 3H), 1.82 (d, 3H), 1.36 (d, 3H). Minor diastereomer: 8.80 (s, 1H), 6.09 (d, 1H), 4.70 (br s, 1H), 3.82 (pentet, 1H), 2.90 (s, 3H), 1.89 (d, 3H), 1.82 (d, 3H), 1.41 (d, 3H). | positive ES MH+ 303/305 |
| A3 | 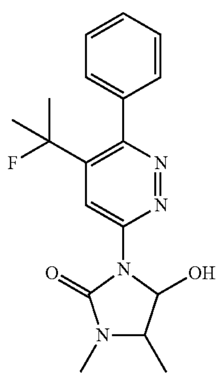 [SMILES: CC1C(O)N(c2cc(C(C)(C)F)c(-c3ccccc3)nn2)C(=O)N1C] | Major diastereomer: 8.71 (s, 1H), 7.45 (m, 3H), 7.39 (m, 2H), 5.80 (s, 1H), 5.18 (br s, 1H), 3.59 (m, 1H), 2.96 (s, 3H), 1.57 (d, 3H), 1.52 (d, 3H), 1.36 (d, 3H). Minor diastereomer: 8.71 (s, 1H), 7.45 (m, 3H), 7.39 (m, 2H), 6.15 (d, 1H), 5.05 (br s, 1H), 3.82 (pentet, 1H), 2.92 (s, 3H), 1.57 (d, 3H), 1.52 (d, 3H), 1.41 (d, 3H). | positive ES MH+ 345 |
| A4 | 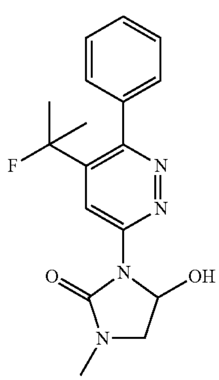 [SMILES: CN1CC(O)N(c2cc(C(C)(C)F)c(-c3ccccc3)nn2)C1=O] | 8.72 (s, 1H), 7.45 (m, 3H), 7.38 (m, 2H), 6.26 (d, 1H), 5.23 (m, 1H), 3.76 (dd, 1H), 3.44 (dd, 1H), 2.98 (s, 3H), 1.56 (d, 3H), 1.52 (d, 3H). | positive ES MH+ 331 |

TABLE 1-continued

| Example | STRUCTURE | 1H NMR (measured in CDCl₃ unless otherwise indicated) δ | LC-MS |
|---------|-----------|---------------------------------------------------------|-------|
| A5 | 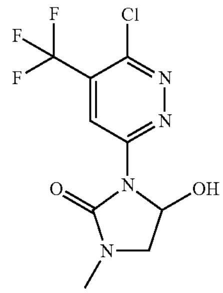 | 8.98 (1H, s), 6.23 (1H, dd), 4.76 (1H, br.s.), 3.80 (1H, dd), 3.47 (1H, dd), 2.99 (3H, s). | positive ES MH+ 297/299 |
| A6 | 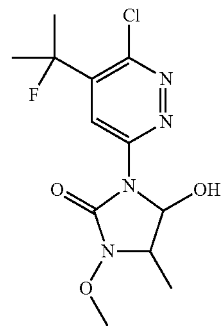 [SMILES: CON1C(=O)N(c2cc(C(C)(C)F)c(Cl)nn2)C(O)C1C] | Major diastereomer: 8.80 1H, 5.68 (m, 1H), 4.95 (br s, 1H), 3.88 (s, 3H), 3.58 (m, 1H), 1.88 (s, 3H), 1.82 (d, 3H), 1.48 (d, 3H). Minor diastereomer: 8.80 (s, 1H), 6.01 (m, 1H), 4.65 (br s, 1H), 3.92 (s, 3H), 3.82 (m, 1H), 1.88 (s, 3H), 1.82 (d, 3H), 1.51 (d, 3H). | positive ES MH+ 319/321 |
| A7 | 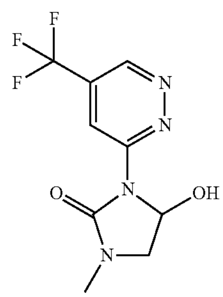 [SMILES: CN1CC(O)N(c2cc(C(F)(F)F)cnn2)C1=O] | 9.06 (d, 1H), 8.84 (m, 1H), 6.26 (dt, 1H), 4.89 (d, 1H), 3.79 (m, 1H), 3.48 (dd, 1H), 2.99 (s, 3H). | positive ES MH+ 263 |
| A8 | 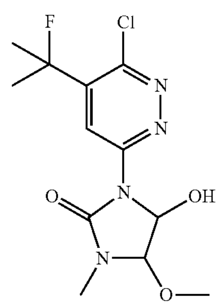 [SMILES: COC1C(O)N(c2cc(C(C)(C)F)c(Cl)nn2)C(=O)N1C] | 8.75 (s, 1H), 5.89 (d, 1H), 5.04 (d, 1H), 4.71 (s, 1H), 3.45 (s, 3H), 3.02 (s, 3H), 1.87 (d, 3H), 1.81 (d, 3H). | positive ES MH+ 319/321 |
| A9 | 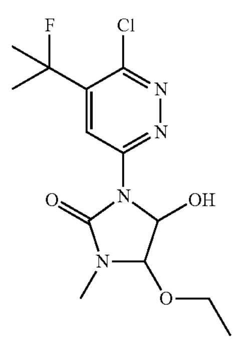 | 8.73 (s, 1H), 5.85 (d, 1H), 4.78 (d, 1H), 4.74 (s, 1H), 3.67 (ddq, 2H), 3.01 (s, 3H), 1.86 (d, 3H), 1.81 (d, 3H), 1.28 (t, 3H). | positive ES MH+ 319/321 |

TABLE 1-continued

| Example | STRUCTURE | 1H NMR (measured in CDCl₃ unless otherwise indicated) δ | LC-MS |
|---|---|---|---|
| A10 | 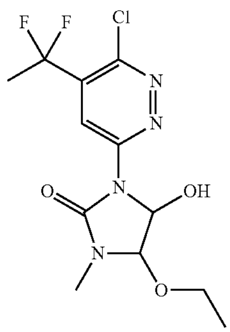 [SMILES: CCOC1C(O)N(c2cc(C(C)(F)F)c(Cl)nn2)C(=O)N1C] | 8.69 (s, 1H), 5.80 (d, 1H), 4.78 (d, 1H), 4.71 (s, 1H), 3.65 (m, 2H), 2.96 (s, 3H), 1.96 (t, 3H), 1.19 (t, 3H). | positive ES MH+ 337/339 |
| A11 | 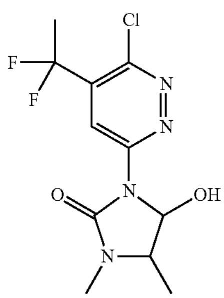 [SMILES: CC1C(O)N(c2cc(C(C)(F)F)c(Cl)nn2)C(=O)N1C] | Major diastereomer: 8.83 (s, 1H), 5.73 (m, 1H), 3.57 (m, 1H), 2.94 (s, 3H), 2.06 (t, 3H), 1.35 (d, 3H). Minor diastereomer: 8.83 (s, 1H), 6.09 (d, 1H), 3.83 (m, 1H), 2.90 (s, 3H), 2.06 (t, 3H), 1.40 (d, 3H). | positive ES MH+ 307/309 |
| A12 | 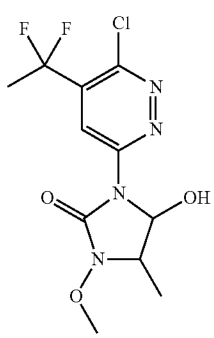 [SMILES: CON1C(=O)N(c2cc(C(C)(F)F)c(Cl)nn2)C(O)C1C] | Major diastereomer: 8.80 (s, 1H), 5.68 (m, 1H), 4.81 (br s, 1H), 3.87 (s, 3H), 3.78 (m, 1H), 2.02 (t, 3H), 1.88 (s, 3H), Minor diastereomer: 8.80 (s, 1H), 6.01 (m, 1H), 4.50 (br s, 1H), 3.92 (s, 3H), 3.82 (m, 1H), 2.02 (t, 3H), 1.48 (d, 3H). | positive ES MH+ 322/325 |
| A13 | 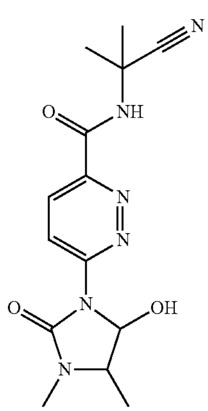 [SMILES: CC1C(O)N(c2ccc(C(=O)NC(C)(C)C#N)nn2)C(=O)N1C] | Major diastereomer: 8.73 (s, 1H), 8.26 (d, 1H), 7.97 (br s, 1H), 5.76 (m, 1H), 4.83 (m, 1H), 3.61 (m, 1H), 2.96 (s, 3H), 1.86 (s, 6H), 1.39 (s, 3H). Minor diastereomer: 8.73 (s, 1H), 8.26 (m, 1H), 7.97 (br s, 1H), 6.15 (m, 1H), 4.66 (m, 1H), 3.86 (m, 1H), 2.92 (s, 3H), 1.86 (s, 6H), 1.43 (m, 3H). | positive ES MH+ 319 |

TABLE 1-continued

| Example | STRUCTURE | 1H NMR (measured in CDCl₃ unless otherwise indicated) δ | LC-MS |
|---|---|---|---|
| A16 | 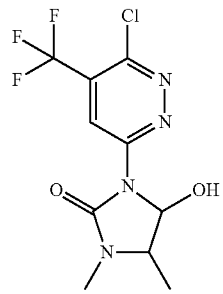 [SMILES: CC1C(O)N(c2cc(C(F)(F)F)c(Cl)nn2)C(=O)N1C] | Major diastereomer: 8.97 (s, 1H), 5.75 (t, 1H), 4.65 (d, 1H), 3.61 (ddd, 1H), 2.95 (s, 3H), 1.38 (d, 3H). Minor diastereomer: 8.97 (s, 1H), 6.11 (dd, 1H), 4.49 (d, H), 3.86 (m, 1H), 2.92 (s, 3H), 1.43 (d, 3H). | positive ES MH+ 311 |
| A17 | 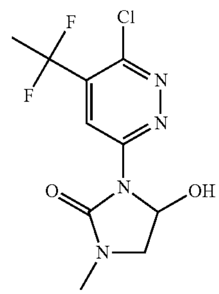 [SMILES: CN1CC(O)N(c2cc(C(C)(F)F)c(Cl)nn2)C1=O] | 8.83 (s, 1H), 6.21 (m, 1H), 4.83 (s, 1H), 3.69-3.87 (m, 1H), 3.46 (dd, 1H), 2.98 (s, 3H), 2.06 (t, 3H). | positive ES MH+ 293 |
| A18 | 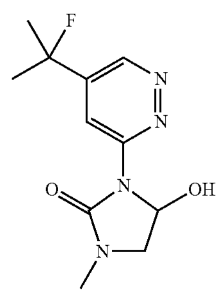 [SMILES: CN1CC(O)N(c2cc(C(C)(C)F)cnn2)C1=O] | 8.93 (d, 1H), 8.49 (dd, 1H), 6.24 (dd, 1H), 5.29 (br s, 1H), 3.76 (dd, 1H), 3.45 (dd, 1H), 2.98 (s, 3H), 1.71 (dd, 6H). | positive ES MH+ 255 |
| A19 | 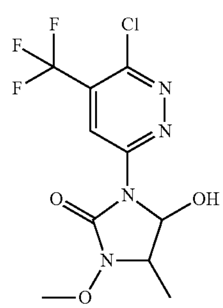 [SMILES: CON1C(=O)N(c2cc(C(F)(F)F)c(Cl)nn2)C(O)C1C] | Major diastereomer: 8.93 (s, 1H), 6.03 (dd, 1H), 4.42 (d, 1H), 3.91 (s, 3H), 3.82 (m, 1H), 1.52 (d, 3H). Minor diastereomer: 8.93 (s, 1H), 5.72 (dd, 1H), 4.72 (d, 1H), 3.94 (s, 3H), 3.37 (d, 1H), 1.48 (d, 3H). | positive ES MH+ 327 |
| A20 | 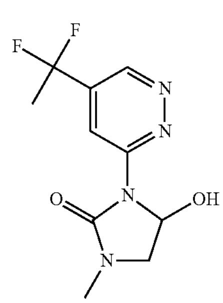 [SMILES: CN1CC(O)N(c2cc(C(C)(F)F)cnn2)C1=O] | 8.98 (d, 1H), 8.59-8.76 (m, 1H), 6.18-6.33 (m, 1H), 5.13 (d, 1H), 3.78 (dd, 1H, ), 3.46 (dd, 1 H), 2.98 (s, 3 H), 1.97 (t, 3 H). | positive ES MH+ 259 |

TABLE 1-continued

| Example | STRUCTURE | 1H NMR (measured in CDCl₃ unless otherwise indicated) δ | LC-MS |
|---|---|---|---|
| A21 | (structure) | Major diastereomer: 9.06 (d, 1H), 8.86 (d, 1H), 5.79 (t, 1H), 4.85 (d, 1H), 3.61 (ddd, 1H), 2.96 (s, 3H), 1.38 (d, 3H). Minor diastereomer: 9.06 (d, 1H), 8.86 (d, 1H), 6.15 (dd, 1H), 4.70 (d, 1H), 3.86 (m, 1H), 2.92 (s, 3H), 1.43 (d, 3H). | positive ES MH+ 277 |
| A22 | (structure) | Major diastereomer: 8.95 (s, 1H), 6.17 (d, 1H), 5.88 (d, 1H), 5.52 (d, 1H), 4.96 (d, 1H), 2.99 (s, 3H). Minor diastereomer: 8.96 (s, 1H), 6.81 (d, 1H), 6.19 (d, 1H), 5.15 (dd, 1H), 4.79 (d, 1H), 2.97 (s, 3H). | positive ES MH+313 |
| A23 | (structure) | 8.90 (s, 1H), 5.88 (d, 1H), 4.76 (s, 1H), 4.64 (d, 1H), 3.70 (m, 2H), 3.02 (s, 3H), 1.29 (t, 3H). | positive ES MH+ 341 |
| A24 | (structure) | 9.06 (d, 1H), 8.80 (d, 1H), 5.95 (s, 1H), 5.11 (br.s., 1H), 4.77 (s, 1H), 3.77-3.63 (m, 2H), 3.03 (s, 3H), 1.29 (t, 3H). | positive ES MH+ 307 |

TABLE 2

| Example | STRUCTURE | LC-MS |
|---|---|---|
| A14 | (structure) | positive ES MH+ 324 |
| A15 | (structure) | positive ES MH+ 308 |

TABLE 2-continued

| Example | STRUCTURE | LC-MS |
|---|---|---|
| A25 | (structure) | positive ES MH+ 294 |

Example 10

Herbicidal Action

Example 10a

Pre-emergence Herbicidal Activity

Seeds of a variety of test species were sown in standard soil in pots. After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 2.

TABLE 3

Application pre-emergence

| Example number | Rate (g/Ha) | AMARE | ABUTH | SETFA | ECHCG | ALOMY | ZEAMX |
|---|---|---|---|---|---|---|---|
| A1 | 1000 | 5 | 5 | 5 | 5 | 4 | 4 |
| A2 | 1000 | 5 | 5 | 5 | 4 | 4 | 3 |
| A3 | 1000 | 5 | 5 | 5 | 4 | 4 | 3 |
| A4 | 1000 | 5 |   | 5 | 5 | 4 |   |
| A5 | 1000 | 5 | 5 | 5 | 4 | 4 | 2 |
| A6 | 1000 | 5 | 5 | 4 | 4 | 3 | 3 |
| A7 | 1000 | 5 | 5 | 5 | 5 | 4 | 2 |
| A8 | 1000 | 5 | 5 | 5 | 5 | 4 | 3 |
| A9 | 1000 | 5 | 5 | 5 | 5 | 4 | 3 |
| A10 | 1000 | 5 | 5 | 5 | 4 | 4 | 4 |
| A11 | 1000 | 5 | 5 | 5 | 5 | 4 | 4 |
| A12 | 1000 | 5 | 5 | 5 | 5 | 3 | 3 |
| A13 | 1000 | 5 | 5 | 4 | 4 | 4 | 3 |

TABLE 3-continued

Application pre-emergence

| Example number | Rate (g/Ha) | AMARE | ABUTH | SETFA | ECHCG | ALOMY | ZEAMX |
|---|---|---|---|---|---|---|---|
| A14 | 1000 | 5 | 5 | 4 | 4 | 4 | 2 |
| A15 | 1000 | 5 | 5 | 4 | 5 | 4 | 3 |
| A16 | 1000 | 5 | 5 | 3 | 5 |   | 3 |
| A18 | 1000 | 5 | 5 | 4 | 5 |   | 2 |
| A20 | 1000 | 5 | 5 | 5 | 5 |   | 3 |
| A21 | 1000 | 5 | 5 | 5 | 5 |   | 3 |
| A22 | 1000 | 5 | 5 | 4 | 2 |   | 1 |
| A23 | 1000 | 5 | 5 | 5 | 5 |   | 2 |
| A24 | 1000 | 5 | 5 | 5 | 4 |   | 2 |
| A25 | 1000 | 5 | 5 | 5 | 5 |   | 2 |

Example 10b

Post-emergence Herbicidal Activity

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 3.

TABLE 4

Application post-emergence

| Example number | Rate (g/Ha) | AMARE | ABUTH | ALOMY | ECHCG | ZEAMX | SETFA |
|---|---|---|---|---|---|---|---|
| A1 | 1000 | 5 | 5 | 5 | 5 | 5 | 5 |
| A2 | 1000 | 5 | 5 | 4 | 5 | 5 | 5 |
| A3 | 1000 | 5 | 5 | 4 | 5 | 4 | 5 |
| A4 | 1000 | 5 | 5 | 5 | 5 | 5 | 5 |
| A5 | 1000 | 5 | 5 | 4 | 5 | 4 | 5 |
| A6 | 1000 | 5 | 5 | 4 | 5 | 5 | 5 |
| A7 | 1000 | 5 | 5 | 5 | 5 | 5 | 5 |
| A8 | 1000 | 5 | 5 | 4 | 5 | 4 | 5 |
| A9 | 1000 | 5 | 5 | 5 | 5 | 5 | 5 |
| A10 | 1000 | 5 | 5 | 5 | 5 | 4 | 5 |
| A11 | 1000 | 5 | 5 | 5 | 5 | 5 | 5 |
| A12 | 1000 | 5 | 5 | 5 | 5 | 3 | 5 |
| A13 | 1000 | 5 | 5 | 4 | 3 | 1 | 5 |
| A14 | 1000 | 5 | 5 | 5 | 5 | 5 | 5 |
| A15 | 1000 | 5 | 5 | 5 | 5 | 5 | 5 |
| A16 | 1000 | 5 | 5 |   | 5 | 3 | 5 |
| A18 | 1000 | 5 | 5 |   | 5 | 4 | 5 |
| A20 | 1000 | 5 | 5 |   | 5 | 5 | 5 |
| A21 | 1000 | 5 | 5 |   | 5 | 5 | 5 |
| A22 | 1000 | 5 | 5 |   | 5 | 3 | 5 |
| A23 | 1000 | 5 | 5 |   | 5 | 3 | 5 |
| A24 | 1000 |   |   |   | 5 |   |   |
| A25 | 1000 | 5 | 5 |   | 5 | 3 | 5 |

ABUTH = *Abutilon theophrasti*; AMARE = *Amaranthus retroflexus*; SETFA = *Setaria faberi*; ALOMY = *Alopecurus myosuroides*; ECHCG = *Echinochloa crus-galli*; ZEAMX = *Zea mays*.

The invention claimed is:
1. A compound of formula (I)

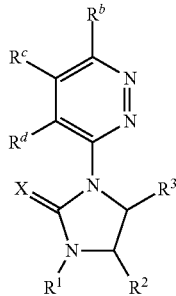

wherein
X is selected from S and O;
$R^b$ is selected from hydrogen, halogen, $C_1$-$C_4$ alkyl, $C_2$-$C_4$ alkenyl, $C_1$-$C_4$ haloalkyl, $C_1$-$C_6$ alkoxy, $C_2$-$C_4$ alkenyloxy, $C_2$-$C_4$ alkynyloxy, $C_1$-$C_4$ alkoxy-$C_1$-$C_4$ alkyl, $C_1$-$C_4$ halolkoxy, $C_1$-$C_3$ alkoxy-$C_1$-$C_3$alkoxy, $C_1$-$C_4$-alkylthio, $C_1$-$C_4$ alkylsulfinyl, $C_1$-$C_4$ alkylsulfonyl, a group $R^5R^6N$—, a group $R^5C(O)N(R^6)$—, a group $R^5S(O_2)N(R^6)$—, a group $R^5R^6NSO_2$—, a group $R^5R^6NC(O)$—, aryl, aryloxy and heteroaryl, where aryl, aryloxy and heteroaryl are optionally substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;
$R^c$ is selected from $C_1$-$C_6$ haloalkyl or, when $R^b$ is $R^5R^6NC(O)$—, $R^c$ is selected from hydrogen, halogen, $C_1$-$C_4$ alkyl and $C_1$-$C_4$ haloalkyl;
$R^d$ is selected from hydrogen, halogen, cyano, $C_1$-$C_6$ alkyl and $C_1$-$C_6$ haloalkyl;
or $R^c$ and $R^d$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;
$R^1$ is selected from hydrogen, hydroxyl, $C_1$-$C_6$ alkyl optionally substituted with $NR^{10}R^{11}$, $C_2$-$C_6$ alkenyl, $C_2$-$C_6$ alkynyl, $C_1$-$C_4$ cycloalkyl, $C_1$-$C_4$ cyanoalkyl, $C_1$-$C_3$ haloalkyl, $C_1$-$C_6$ alkoxy and $C_1$-$C_4$ alkoxy-$C_1$-$C_4$ alkyl; wherein $R^{10}$ and $R^{11}$ are independently selected from hydrogen, $C_1$-$C_6$ alkyl and $C_1$-$C_6$ haloalkyl;
$R^2$ is selected from hydrogen, hydroxyl, halogen, $C_1$-$C_6$ alkyl, $C_2$-$C_6$ alkenyl, $C_2$-$C_6$ alkynyl, $C_1$-$C_6$ alkoxy, $C_2$-$C_6$ alkenyloxy, $C_2$-$C_6$ alkynyloxy, $C_{1\text{-}C6}$ haloalkyl, $C_1$-$C_6$ haloalkoxy, $C_{1\text{-}C6}$ alkoxy $C_1$-$C_6$ alkyl, $C_1$-$C_4$ alkoxy-$C_1$-$C_4$ alkoxy, $C_1$-$C_4$ hydroxyalkyl, $C_1$-$C_6$ cyanoalkyl and the group —$NR^{12}R^{13}$, wherein $R^{12}$ and $R^{13}$ are independently selected from hydrogen and $C_1$-$C_6$ alkyl;
or $R^1$ and $R^2$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from hydroxyl, =O, $C_1$-$C_6$ alkyl and $C_1$-$C_6$ haloalkyl;

$R^3$ is selected from halogen, hydroxyl, —$NR^{14}R^{15}$ or any one of the following groups

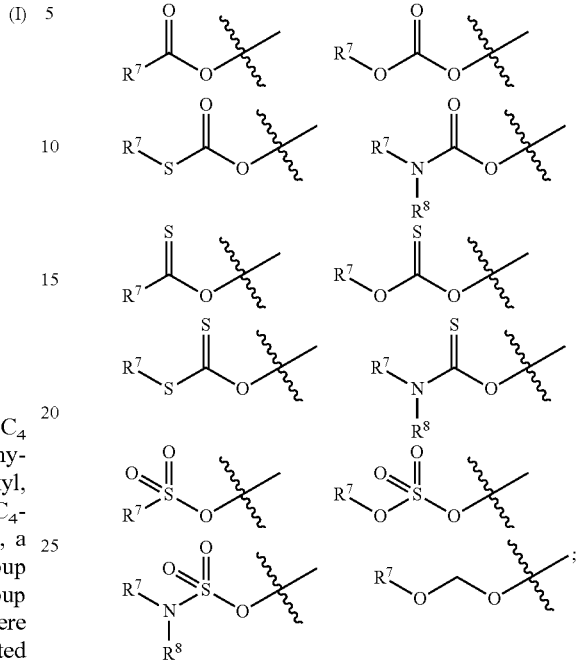

$R^5$ and $R^6$ are independently selected from hydrogen, $C_1$-$C_6$ alkyl, $C_1$-$C_6$ haloalkyl, $C_1$-$C_6$ cyanoalkyl, $C_2$-$C_6$ alkenyl, $C_2$-$C_6$ alkynyl, $C_1$-$C_6$ alkoxy and $C_1$-$C_6$ alkoxy-$C_1$-$C_6$ alkyl or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;
$R^7$ and $R^8$ are independently selected from
hydrogen, $C_1$-$C_6$ alkyl, $C_1$-$C_6$ haloalkyl, $C_2$-$C_6$ alkenyl, $C_2$-$C_6$ alkynyl,
a $C_3$-$C_6$ cycloalkyl group optionally substituted with 1 to 3 groups independently selected from $C_1$-$C_3$ alkyl, $C_2$-$C_4$ alkenyl, $C_1$-$C_3$ haloalkyl and $C_2$-$C_4$ haloalkenyl,
a $C_5$-$C_{10}$ heterocyclyl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy,
a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy,
a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy,
a $C_6$-$C_{10}$ arylalkyl group optionally substituted with 1 to 3 groups independently selected from $C_1$-$C_4$ alkyl, $C_1$-$C_3$ alkoxy, $C_1$-$C_3$ haloalkyl and the group —OC(O)—$C_1$-$C_4$ alkyl, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

$R^9$ is selected from $C_1$-$C_6$ alkyl and benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;

$R^{14}$ and $R^{15}$ are, independently, selected from hydrogen, $C_1$-$C_{20}$ alkyl, $C_1$-$C_{20}$ haloalkyl, $C_1$-$C_{20}$ alkoxy, $C_1$-$C_{20}$ alkoxy-$C_1$-$C_{20}$ alkyl, $C_2$-$C_{20}$ alkenyl, $C_2$-$C_{20}$ alkynyl and benzyl, or $R^{14}$ and $R^{15}$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

or an N-oxide or salt form thereof.

2. The compound of claim 1, wherein X is O.

3. The compound of claim 1, wherein $R^b$ is selected from hydrogen, halogen, methoxy, $R^5R^6NC(O)$—, heteroaryl substituted by halogen or methoxy groups and aryl substituted by halogen or methoxy groups.

4. The compound of claim 1, wherein $R^c$ is selected from 1,1-difluoroethyl, difluoromethyl, 1-fluoro-1-methylethyl or trifluoromethyl, or, when $R^b$ is $R^5R^6NC(O)$—, $R^c$ is selected from hydrogen, Cl and trifluoromethyl.

5. The compound of claim 4, wherein $R^c$ is selected from 1,1-difluoroethyl, 1-fluoro-1-methylethyl and trifluoromethyl.

6. The compound of claim 1, wherein $R^d$ is hydrogen.

7. The compound of claim 1, wherein $R^1$ is selected from $C_1$-$C_3$ alkyl, $C_1$-$C_3$ alkoxy and $C_1$-$C_3$ haloalkyl.

8. The compound of claim 1, wherein $R^2$ is selected from hydrogen, hydroxyl, $C_1$-$C_3$ alkyl, $C_1$-$C_3$ alkoxy, $C_1$-$C_3$ haloalkyl and $C_1$-$C_3$ alkoxy-$C_1$-$C_3$ alkyl.

9. The compound of claim 1, wherein $R^3$ is selected from halogen, hydroxyl, and any of the following groups

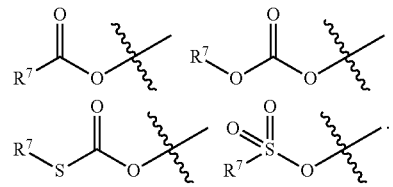

10. A herbicidal composition comprising a compound of formula I as defined in claim 1 together with an agriculturally acceptable adjuvant or diluent.

11. The composition of claim 10 further comprising an additional herbicide compound in addition to the compound of formula I.

12. The composition of claim 10 further comprising a safener.

13. A method of controlling weeds in crops of useful plants, comprising applying to said weeds or to a locus of said weeds, or to said useful plants or to a locus of said useful plants, a compound of formula I as defined in claim 1.

* * * * *